United States Patent
Kauper et al.

(10) Patent No.: US 9,265,814 B2
(45) Date of Patent: *Feb. 23, 2016

(54) MICRONIZED DEVICE FOR THE DELIVERY OF BIOLOGICALLY ACTIVE MOLECULES AND METHODS OF USE THEREOF

(75) Inventors: Konrad Kauper, Sutton, MA (US); Weng Tao, Lincoln, RI (US); Paul Stabila, Coventry, RI (US)

(73) Assignee: Neurotech USA, INC., Cumberland, RI (US)

( * ) Notice: Subject to any disclaimer, the term of this patent is extended or adjusted under 35 U.S.C. 154(b) by 2154 days.

This patent is subject to a terminal disclaimer.

(21) Appl. No.: 12/087,089

(22) PCT Filed: Dec. 18, 2006

(86) PCT No.: PCT/US2006/048292
§ 371 (c)(1),
(2), (4) Date: May 18, 2011

(87) PCT Pub. No.: WO2007/078922
PCT Pub. Date: Jul. 12, 2007

(65) Prior Publication Data
US 2011/0236457 A1    Sep. 29, 2011

Related U.S. Application Data

(60) Provisional application No. 60/755,478, filed on Dec. 30, 2005.

(51) Int. Cl.
| | | |
|---|---|---|
| *A61K 38/00* | (2006.01) | |
| *A61K 48/00* | (2006.01) | |
| *A61K 49/00* | (2006.01) | |
| *A01N 63/00* | (2006.01) | |
| *A61K 38/57* | (2006.01) | |
| *A61K 9/00* | (2006.01) | |
| *A61K 38/18* | (2006.01) | |
| *A61K 38/20* | (2006.01) | |
| *A61K 35/12* | (2015.01) | |

(52) U.S. Cl.
CPC .............. *A61K 38/57* (2013.01); *A61K 9/0048* (2013.01); *A61K 9/0051* (2013.01); *A61K 38/185* (2013.01); *A61K 38/2066* (2013.01); *A61K 2035/128* (2013.01)

(58) Field of Classification Search
CPC . A61K 2300/00; A61K 38/57; A61K 9/0051; A61K 2035/128; A61K 9/0048; A61K 38/185; A61K 38/2066; A61K 38/18; A61K 35/30; A61K 38/00; C12Q 1/6883; A61B 6/4057; A61F 9/00; A61L 27/3813; A61L 27/3869; A61L 27/52; A61L 27/56; C12N 5/0621; C07K 14/475; C07K 14/71
See application file for complete search history.

(56) References Cited

U.S. PATENT DOCUMENTS

| | | | |
|---|---|---|---|
| 3,615,024 A | 10/1971 | Michaels | 210/490 |
| 4,352,833 A | 10/1982 | Young et al. | 427/4 |
| 4,409,331 A | 10/1983 | Lim | 435/178 |
| 4,744,933 A | 5/1988 | Rha et al. | 264/4.3 |
| 4,892,538 A | 1/1990 | Aebischer et al. | 604/891.1 |
| 4,968,733 A | 11/1990 | Müller et al. | 521/64 |
| 4,976,859 A | 12/1990 | Wechs | 210/500.23 |
| 5,002,661 A | 3/1991 | Chick et al. | 210/192 |
| 5,049,493 A | 9/1991 | Khosla et al. | 435/69.1 |
| 5,082,670 A | 1/1992 | Gage et al. | 424/520 |
| 5,156,844 A | 10/1992 | Aebischer et al. | 424/424 |
| 5,158,881 A | 10/1992 | Aebischer et al. | 435/182 |
| 5,167,762 A | 12/1992 | Carr et al. | 156/657 |
| 5,283,187 A | 2/1994 | Aebischer et al. | 435/182 |
| 5,284,761 A | 2/1994 | Aebischer et al. | 435/182 |
| 5,512,600 A | 4/1996 | Mikos et al. | 521/61 |
| 5,550,050 A | 8/1996 | Holland et al. | 435/240.2 |
| 5,639,275 A | 6/1997 | Baetge et al. | 604/891.1 |
| 5,653,688 A | 8/1997 | Mills et al. | 604/57 |
| 5,653,975 A | 8/1997 | Baetge et al. | 424/93.1 |
| 5,713,887 A | 2/1998 | Mills et al. | 604/890.1 |
| 5,738,673 A | 4/1998 | Mills et al. | 604/891.1 |
| 5,762,798 A | 6/1998 | Wenthold et al. | 210/500.23 |
| 5,932,460 A | 8/1999 | Mills et al. | 435/182 |
| 6,123,700 A | 9/2000 | Mills et al. | 604/890.1 |
| 6,267,954 B1 | 7/2001 | Abitbol et al. | |
| 6,303,136 B1 | 10/2001 | Li et al. | 424/424 |
| 6,361,771 B1 | 3/2002 | Tao et al. | 424/93.21 |
| 6,627,422 B1 | 9/2003 | Li et al. | 435/182 |
| 6,653,687 B1 | 11/2003 | Yamazaki | 257/345 |
| 2005/0089960 A1 | 4/2005 | Wahlberg et al. | 435/69.1 |

(Continued)

FOREIGN PATENT DOCUMENTS

| | | |
|---|---|---|
| WO | WO 91/00119 | 1/1991 |
| WO | WO 92/03327 | 5/1992 |

(Continued)

OTHER PUBLICATIONS

Sieving et al. Invest. Ophthalmol. Vis. Sci. May 1, 2005; 46; E-Abstract 531.*

(Continued)

*Primary Examiner* — Chang-Yu Wang

(74) *Attorney, Agent, or Firm* — Cooley, LLP; Ivor Elrifi; Christina Stock

(57) ABSTRACT

The invention provides micronized encapsulated cell therapy devices that are capable of delivering a biologically active molecule to the eye. Also provided are methods of using the same to deliver biologically active molecules to the eye and to treat ophthalmic disorders in patients suffering there from.

4 Claims, 15 Drawing Sheets

(56) References Cited

U.S. PATENT DOCUMENTS

| | | | |
|---|---|---|---|
| 2005/0180957 A1 | 8/2005 | Scharp et al. | 424/93.7 |
| 2005/0287320 A1 | 12/2005 | Dalton et al. | 428/34.1 |

FOREIGN PATENT DOCUMENTS

| | | |
|---|---|---|
| WO | WO 92/19195 | 11/1992 |
| WO | WO 93/00128 | 1/1993 |
| WO | WO 93/03901 | 3/1993 |
| WO | WO 95/05452 | 2/1995 |
| WO | WO 97/34586 | 9/1997 |
| WO | WO 98/43177 | 10/1998 |
| WO | WO 99/52573 | 10/1999 |
| WO | WO-2005110436 A2 | 11/2005 |

OTHER PUBLICATIONS

Tao et al. Invest. Ophthalmol. Vis. Sci. May 2005; 46: E-Abstract 497.*

Thanos et al. Tissue Engineering 2004, 10: 1617-1622.*

Bush et al. Inves. Ophthalmol. Vis. Sci. 2004; 45:2420-2430.*

Sieving. "Ciliary Neurotropic Factor (CNTF) for Human Retinal Degeneration: Phase I of CNTF Delivered by Encapsulated Cell Intraocular Implants." *PNAS.* 103.10(2006):3896-3901.

Thanos et al. "Sustained Secretion of Ciliary Neurotrophic Factor to the Vitreous, Using the Encapsulated Cell Therapy-Based NT-501 Intraocular Device." *Tissue Eng.* 10,11-12(2004):1617-1622.

Baetge et al., "Transgenic mice express the human phenylethanolamine N-methyltransferase gene in adrenal medulla and retina", *Proc. Natl. Acad. Sci. USA*, 85:3648-3652 (1988).

Besnard et al., "Multiple Interacting Sites Regulate Astrocyte-specific Transcription of the Human Gene for Glial Fibrillary Acidic Protein" *J. Biol. Hem.*, 266(28):18877-18883 (1991).

Cepko, C.L., "Retrovirus Vectors and Their Applications in Neurobiology" *Neuron*, 1:345-353 (1988).

Chick et al., "A transplantable insulinoma in the rat" *Proc. Natl. Acad. Sci. USA*, 74:628-632 (1977).

Christenson et al., "Tissue reaction to intraperitoneal polymer implants: Species difference and effects of corticoid and doxorubicin" *J. Biomed. Mat. Res.*, 23:705-718 (1989).

Christenson, L., "Polymer-encapsulated thymic stromal tissue: Biocompatibility, procurement and functional studies" Dissertation, Brown University, pp. 1-119 (1990).

Colton, "Engineering challenges in cell-encapsulation technology" *Trends Biotechnol.*, 14:158-162 (1996).

Dirks et al., "Dicistronic transcription units for gene expression in mammalian cells" *Gene*, 128:247-249 (1993).

Dunn et al., "ARPE-19, A Human Retinal Pigment Epithelial Cell Line with Differentiation Properties" *Exp. Eye Res.*, 62:155-169 (1996).

Dunn et al., "Use of the ARPE-19 Cell Line as a Model of RPE Polarity: Basolateral Secretion of FGF5" *Invest. Ophthalmol. Vis. Sci.*, 39:2744-2749 (1998).

Faithful, N.S., "Fluorocarbons" *Anaesthesia*, 42:234-242 (1987).

Finnemann et al., "Phagocytosis of rod outer segments by retinal pigment epithelial cells requires $\alpha v \beta 5$ integrin for binding but not for internalization" *Proc. Natl. Acad. Sci. USA*, 94:12932-12937 (1997).

Gale Group Newsletter DB™, "Regeneron's Neurotrophic Factors Prevent Degeneration of Eye Retina Cells" *Genetic Technology News*, vol. 13, No. 1, 2 pages (1993).

Hamaguchi et al., "NIT-1, a Pancreatic β-Cell Line Established From a Transgenic NOD/Lt Mouse" *Diabetes*, 40:842-849 (1991).

Handa et al., "The Advanced Glycation Endproduct Pentosidine Induces the Expression of PDGF-B in Human Retinal Pigment Epithelial Cells" *Exp. Eye Res.*, 66:411-419 (1998).

Holtkamp et al., "Polarized secretion of IL-6 and IL-8 by human retinal pigment epithelial cells" *Clin. Exp. Immunol.*, 112:34-43 (1998).

Hughes et al., "Engineering of glucose-stimulated insulin secretion and biosynthesis in non-islet cells" *Proc. Natl. Acad. Sci. USA*, 89:688-692 (1992).

Kaneda et al., "Tissue-Specific and High-Level Expression of the Human Tyrosine Hydroxylase Gene in Transgenic Mice" *Neuron*, 6:583-594 (1991).

Land et al., "Tumorigenic conversion of primary embryo fibroblasts requires at least two cooperating oncognenes" *Nature*, 304:596-602 (1983).

Lemke et al., "Isolation and Analysis of the Gene Encoding Peripheral Myelin Protein Zero" *Neuron*, 1:73-83 (1988).

Lim et al., "Microencapsulated Islets as Bioartificial Endocrine Pancreas" *Science*, 210:908-910 (1980).

Lysaght et al., "Recent Progress in Immunoisolated Cell Therapy" *J. Cell. Biochem.*, 56:196-203 (1996).

Macejak, "Internal initiation of translation mediated by the 5' leader of a cellular mRNA" *Nature*, 353:90-94 (1991).

Maidji et al., "Accessory Human Cytomegalovirus Glycoprotein US9 in the Unique Short Component of the Viral Geome Promotes Cell-to-Cell Transmission of Virus in Polarized Epithelial Cells" *J. Virol.*, 70:8402-8410 (1996).

Martinez-Salas et al., "A Single Nucleotide Substitution in the Internal Ribosome Entry Site of Foot-and-Mouth Disease Virus Leads to Enhanced Cap-Independent Translation In Vivo".,*J. Virol.*, 67:3748-3755 (1993).

Matsumoto et al., "Human macrophage scavenger receptors: Primary structure, expression, and localization in atherosclerotic lesions" *Proc. Natl. Acad. Sci. USA*, 87:9133-9137 (1990).

Mercer et al., "The Dopamine β-Hydroxylase Gene Promoter Directs Expression of *E. coli lacZ* to Sympathetic and other Neurons in Adult Transgenic Mice" *Neuron*, 7:703-716 (1991).

Mountford et al., "Dicistronic targeting constructs: Reporters and modifiers of mammalian gene expression" *Proc. Natl. Acad. Sci. USA*, 91:4303-4307 (1994).

Mountford et al., "Internal ribosome entry sites and dicistronic RNAs in mammalian transgenesis" *Trends Genet.*, 11:179-184 (1995).

Nakahira et al., "Structure of the 68-kDa Neurofilament Gene and Regulation of Its Expression" *J. Biol. Hem.*, 265:19786-19791 (1990).

NASA Tech. Briefs, "Emulsions Containing Perfluorocarbon Support Cell Cultures" MSC-21480, Technical Support Package, U.S. Government Printing Office, Washington, D.C. 5 pages.

NASA Tech. Briefs, "Cloned Hemoglobin Genes Enhance Growth of Cells" NPO-17517/7027, Technical Support Package, Khosla and Bailey (inventors), vol. 15, No. 1, Item #113, pp. 54, 1, 1a, 1b-29b (1991).

Rajotte et al., "Optimizing Cryopreservation of Isolated Islets" *Transplantation Proceedings*, 21(1):2638-2640 (1989).

Ray et al., "Proliferation, differentiation, and long-term culture of primary hippocampal neurons" *Proc. Natl. Acad. Sci. USA*, 90:3602-3606 (1993).

Richards et al., "De novo generation of neuronal cells from the adult mouse brain" *Proc. Natl. Acad. Sci. USA*, 89:8591-8595 (1992).

Sakimura et al., "The structure and expression of neuron-specific enolase gene" *Gene*, 60:103-113 (1987).

Scharp et al., "Islet Immuno-isolation: The Use of Hybrid Artificial Organs to Prevent Islet Tissue Rejection" *World J. Surg.*, 8:221-229 (1984).

Siliprandi et al., "Nerve Growth Factor Promotes Functional Recovery of Retinal Ganglion Cells After Ischemia" *Invest. Ophthalmol. Vis. Sci.*, 34:3232-3245 (1993).

Southern, P.J., "Mammalian Cell Transformation With SV Hybrid Plasmid Vectors" *In Vitro*, 18:315 (1981).

Southern et al., "Transformation of Mammalian Cells to Antibiotic Resistance with a Bacterial Gene Under Control of the SV40 Early Region Promoter" *J. Mol. Appl. Genet.*, 1:327-341 (1982).

Sun, A.M., "Microencapsulation of Pancreatic Islet Cells: A Bioartificial Endocrine Pancreas" *Meth. Enzymol.*, 137:575-579 (1988).

Tal et al., "Glucose Transporter Isotypes Switch in T-Antigen-Transformed Pancreatic β Cells Growing in Culture and in Mice" *Mol. Cell Biol.*, 12:422-432 (1992).

Wilson et al., "The Oxygen Dependence of Mitochondrial Oxidative Phosphorylation Measured by a New Optical Method for Measuring Oxygen Concentration" *J. Biol. Chem.*, 263:2712-2718 (1988).

* cited by examiner

MICRONIZED DEVICE FOR THE DELIVERY OF BIOLOGICALLY ACTIVE MOLECULES AND METHODS OF USE THEREOF

RELATED APPLICATIONS

This application is a 35 U.S.C. §371 filing of PCT Application No. PCT/US2006/048292, filed Dec. 18, 2006, which claims priority to U.S. Ser. No. 60/755,478, filed on Dec. 30, 2005, each is herein incorporated by reference in its entirety.

FIELD OF THE INVENTION

The present invention relates generally to the field of encapsulated cell therapy.

BACKGROUND OF THE INVENTION

Many clinical conditions, deficiencies, and disease states can be remedied or alleviated by supplying to the patient one or more biologically active molecules produced by living cells or by removing from the patient deleterious factors which are metabolized by living cells. In many cases, these molecules can restore or compensate for the impairment or loss of organ or tissue function. Accordingly, many investigators have attempted to reconstitute organ or tissue function by transplanting whole organs, organ tissue, and/or cells, which provide secreted products or affect metabolic functions. However, while transplantation can provide dramatic benefits, it is limited in its application by the relatively small number of organs that are suitable and available for grafting. In general, transplantation patients must be immunosuppressed in order to avert immunological rejection of the transplant, which results in loss of transplant function and eventual necrosis of the transplanted tissue or cells. Likewise, in many cases, the transplant must remain functional for a long period of time, even for the remainder of the patient's lifetime. It is both undesirable and expensive to maintain a patient in an immunosuppressed state for a substantial period of time.

A number of vision-threatening disorders of the eye exist for which additional good therapies are still needed. One major problem in treatment of such diseases is the inability to deliver therapeutic agents into the eye and to maintain them there at therapeutically effective concentrations.

Many growth factors have shown promise in the treatment of ocular disease. For example, BDNF and CNTF have been shown to slow degeneration of retinal ganglion cells and decrease degeneration of photoreceptors in various animal models. See, e.g., Genetic Technology News, vol. 13, no. 1 (January 1993). Additionally, nerve growth factor has been shown to enhance retinal ganglion cell survival after optic nerve section and has also been shown to promote recovery of retinal neurons after ischemia. See, e.g., Siliprandi, et al., Invest. Ophthalmol. & Vis. Sci., 34, pp. 3232-3245 (1993).

A desirable alternative to transplantation procedures is the implantation of cells or tissues within a physical barrier which will allow diffusion of nutrients, metabolites, and secreted products, but will block the cellular and molecular effectors of immunological rejection. A variety of macrocapsule devices which protect tissues or cells producing a selected product from the immune system have been explored. See, e.g., U.S. Pat. No. 5,158,881; WO92/03327; WO91/00119; and WO93/00128, each of which is incorporated herein by reference in its entirety. These devices include, for example, extravascular diffusion chambers, intravascular diffusion chambers, intravascular ultrafiltration chambers, and implantation of microencapsulated cells. See Scharp, D. W., et al., World J. Surg.,. 8, pp. 221-9 (1984). See, e:g., Lim et al., Science 210: 908-910 (1980); Sun, A. M., Methods in Enzymology 137: 575-579 (1988.); WO 93/03901; and U.S. Pat. No. 5,002,661. Such devices would alleviate the need to maintain the patient in an immunosuppressed state. However, none of these approaches have been satisfactory for providing long-term transplant function.

Thus, methods of delivering appropriate quantities of needed substances, such as, neurotrophic factors, anti-angiogenic factors, anti-inflammatory factors, enzymes, hormones, other factors or, of providing other needed metabolic functions, to the eye for an extended period of time are needed.

SUMMARY OF THE INVENTION

The invention provides micronized devices for the delivery of a biologically active molecule to the eye. Such micronized devices contain a capsule having a core containing between about $5 \times 10^2$ and $90 \times 10^3$ living cells that produce a biologically active molecule and a biocompatible jacket surrounding said core, wherein the jacket has a molecular weight cutoff permitting diffusion of the biologically active molecule into the eye. Preferably, the device is configured as a cylinder with an outer diameter of between 200 and 350 µm and a length of between 0.5 and 6 mm. The dosage of the biologically active molecule that diffuses into the eye is between 0.1 pg and 1000 ng per eye per patient per day. In various embodiments, the BAM dosage may be between 0.1 pg and 500 ng per eye per patient per day; between 0.1 pg and 250 ng, between 0.1 pg and 100 ng, between 0.1 pg and 50 ng, between 0.1 pg and 25 ng, between 0.1 pg and 10 ng, or between 0.1 pg and 5 ng per eye per patient per day.

In some embodiments, the micronized device may optionally have a tether adapted for securing the capsule to an ocular structure. For example, the tether may be selected from a loop, a disk, and/or a suture. Such tethers can be made from a shape memory material or any other medical grade material known to those skilled in the art.

The jacket of the micronized devices of the invention may be a permselective, immunoisolatory membrane. Moreover, the biocompatible jacket can be made from either an ultrafiltration or a microporous membrane. Typically, the jacket is made from a polymer material. Suitable polymer materials include, but are not limited to, polyacrylonitrile-polyvinylchloride, polyacrylonitrile, polymethylmethacrylate, polyvinyldifluoride, polyolefins, polysulfones, polymide, and/or celluloses.

The micronized devices of the invention can be implanted in the vitreous, the Sub-Tenon's capsule, the periocular space, and/or the anterior chamber.

Suitable biologically active molecules include, but are not limited to, antiangiogenic factors, anti-inflammatory factors, neurotrophic factors, growth factors, trophic factors, antibodies and antibody fragments, neurotransmitters, hormones, cytokines, and lymphokines. In some embodiments, the biologically active molecule is a cytokine or a lymphokine such as TGFβ, GDNF, NGF, CNTF, bFGF, aFGF, IL-1β, IFN-β, IFN-α, BDNF, LIF, NT-4, NTN, NT4/5, CT-1, LEDGF, Neublastin, Axokine, IL-23, RdCVF, IL-10, Alpha INF, IL-1Rα, and/or Remicade. In other embodiments, the biologically active molecule is an antiangiogenic factor such as vasculostatin, angiostatin, endostatin, anti-integrins, vascular endothelial growth factor inhibitors (VEGF-inhibitors), platelet factor 4, heparinase, bFGF-binding molecules, the VEGF receptor Flt, the VEGF receptor Flk, Lucentis, VEGF Trap, Tek Δ/Fc (ang1/ang2 inhibitor), 2xCon4 (C), soluble VEGF Receptors, and PEDF.

In further embodiments, at least one additional biologically active molecule is delivered from the capsule to the eye. The additional biologically active molecule or molecules may be from a cellular source or from a noncellular source. When the at least one additional biologically active molecule is from a noncellular source, it can be encapsulated in, dispersed within, or attached to one or more components of the micronized device. By way of nonlimiting example, the at least one additional biologically active molecule from a noncellular source can be selected from nucleic acids, nucleic acid fragments, peptides, polypeptides, peptidomimetics, carbohydrates, lipids, organic molecules, inorganic molecules, therapeutic agents, and various combinations thereof. Suitable therapeutic agents include, but are not limited to, anti-angiogenic drugs, steroidal and non-steroidal anti-inflammatory drugs, anti-mitotic drugs, anti-tumor drugs, anti-parasitic drugs, IOP reducers, peptide drugs, and other biologically active molecule drugs approved for ophthalmologic use.

The living cells contained within the core of the micronized devices of the invention may include insulin-producing cells, adrenal chromaffin cells, antibody-secreting cells, fibroblasts, astrocytes, Beta cell lines, Chinese hamster ovary cells, and/or ARPE-19 cells. These cells may be allogeneic and/or syngeneic.

The molecular weight cut off of the biocompatible jacket of the micronized device of the invention is between about 1 kD and about 150 kD.

In some embodiments, the core of the micronized device has a volume of less than 0.5 µl. The core may also contain a substantially non-degradable filamentous cell-supporting matrix, wherein the matrix is made from a plurality of monofilaments, and wherein the monofilaments are either twisted into a yarn or woven into a mesh or twisted into a yarn that is in non-woven strands. The cells in the core can be distributed on the non-degradable filamentous cell-supporting matrix. Suitable filamentous cell-supporting matrices include, but are not limited to, biocompatible materials selected from acrylic, polyester, polyethylene, polypropylene polyacetonitrile, polyethylene terephthalate, nylon, polyamides, polyurethanes, polybutester, silk, cotton, chitin, carbon, and biocompatible metals.

The invention also provides methods for delivering a biologically active molecule to the eye by implanting at least one micronized device according to the invention into the eye or surrounding the eye and allowing said biologically active molecule to diffuse from the device into the vitreous, the aqueous humor, or the periocular space. Optionally, the implantation can be accomplished using a syringe.

Also provided are methods of treating ophthalmic disorders in patients suffering therefrom by implanting one or more of the micronized devices of the invention into an eye of the patient. For example, the ophthalmic disorder to be treated may be a retinal degeneration disease such as retinopathy of prematurity, glaucoma, cataract formation, retinoblastoma, retinal ischemia, uveitis, retinitis pigmentosa, forms of wet and dry age-related macular degeneration, diabetic retinopathy, and/or choroideremia.

The invention also provides for the use of the micronized devices of the invention in the manufacture of medicaments for treating ophthalmic disorders in patient suffering therefrom by implanting the device into an eye of the patient. For example, the ophthalmic disorder can be a retinal degeneration disease selected from retinopathy of prematurity, glaucoma, cataract formation, retinoblastoma, retinal ischemia, uveitis, retinitis pigmentosa, forms of wet and dry age-related macular degeneration, diabetic retinopathy, and/or choroideremia.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1A shows the delivery of device through 30 gauge needle. FIG. 1B shows the delivery of the device using canulated titanium rod. FIG. 1C shows an 11-0 suture embedded into the adhesive end of the micronized device.

FIG. 3A shows that the attachment of cells to the inner wall of the polyimide membrane result in eventual cell death due to restricted diffusion. In contrast, FIG. 3B shows that the polysulfone membranes create a 10 +micron separation between the inner wall and the encapsulated cell mass, thereby allowing effective diffusion to maintain cell viability.

FIG. 14A shows CNTF levels produced in vitro over course of 8 weeks. FIG. 14B shows the results of experiments where metabolic activity of encapsulated cells over an 8 week period was quantified by a cell redox assay (CCK-8). FIG. 14C shows in vivo explant device CNTF levels at 2 and 4 week time points. FIG. 14D shows explant vitreous CNTF levels at both 2 and 4 weeks.

DETAILED DESCRIPTION OF THE INVENTION

The instant invention relates to micronized biocompatible, optionally immunoisolatory, devices for the delivery of one or more biologically active molecules ("BAMs") to the eye. More particularly, such micronized devices contain a core containing living cells that produce or secrete the BAM and a biocompatible jacket surrounding the core, wherein the jacket has a molecular weight cut off ("MWCO") that allows the diffusion of the BAM into the eye.

This invention further relates to delivery of the BAMs intraocularly (e.g., in the anterior chamber and the vitreous cavity) or periocularly (e.g., within or beneath Tenon's capsule), or both. The invention may also be used to provide controlled and sustained release of biologically active molecules effective in treating various ophthalmic disorders, ophthalmic diseases and/or diseases which have ocular effects.

The use of biologically compatible polymeric materials in the construction of a micronized encapsulation device is critical to the success of cell encapsulation therapy ("ECT"). Important components of the encapsulation device include the surrounding semi-permeable membrane as well as the internal cell-supporting matrix or scaffold.

Figure 1:
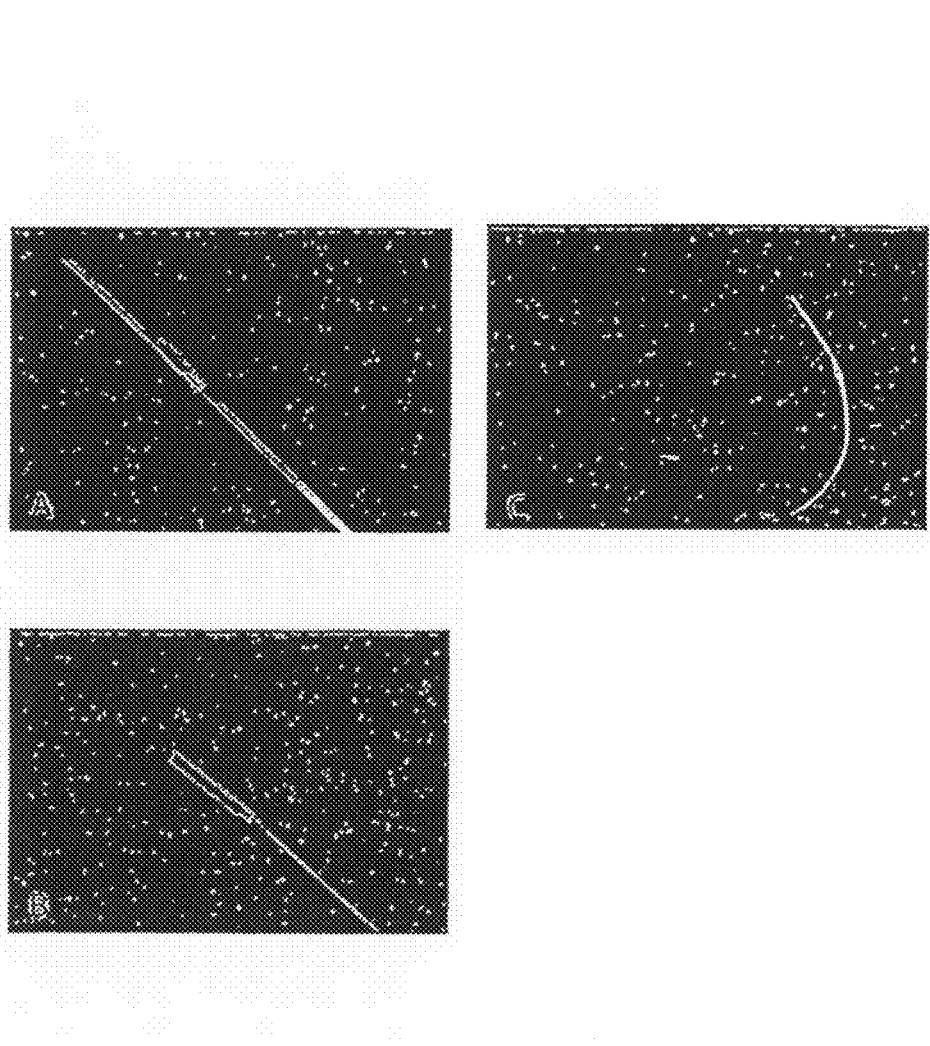
FIG. 1 is a series of photographs of micronized ECT devices and the suture attachment points used to facilitate surgical insertion and scleral attachment in the eye of a rodent.

Micronized ECT devices were fabricated using 50 kDa molecular weight cut-off dialysis membranes having a 200 micron diameters and an overall implant length of 1 millimeter. Total displaced volume of such devices was less than about 0.5 microliters (for example, about 0.3 μl), which represents a volume reduction of more than 200 fold compared to the current human clinical ECT devices (referred to herein as "the first generation ECT devices and/or "the first generation devices"). Implant device configurations for the micronized devices of the invention were developed to facilitate insertion and attachment to the sclera. (See FIG. 1).

Those skilled in the art will recognize that the terms "micronized device(s)", "micronized ECT device(s)", "microdevice(s)", and "micro-ECT device(s)" and the like are used interchangeably herein to refer to the encapsulated cell therapy devices of the instant invention.

Suitable device membranes were manufactured using either polysulfone/polyvinyl pyrrolidone or polyimide. Various cell scaffolding matrices were investigated for their ability to induce cell attachment and cell growth and to sustain cell viability. Scaffolding matrices that were tested included, for example, alginate cross-linked with CaCl, Matrigel, Purapeptide, and non-degradable microspheres with and without fibronectin. Moreover, encapsulation using a PET monofilament yarn matrix was also investigated. Various combinations of membrane and scaffolding were evaluated and compared to devices encapsulated with engineered human retinal pigment epithelial cells (ARPE-19) producing either CNTF or IL-10. Protein secretion over the course of the in vitro evaluation period was quantified by ELISA. The viability of the encapsulated cells was evaluated using a DNA assay to determine total cell number, metabolic activity using a redox assay, nuclear fluorescent labeling of live cells, apoptotic cytohistochemistry and histological examination of sectioned devices. Additionally, various micronized devices were implanted in the rodent vitreous and clinically evaluated.

Figure 2:
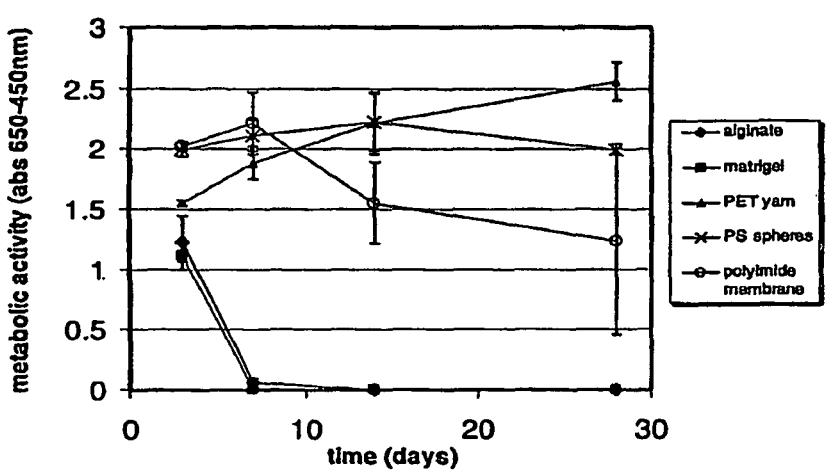
FIG. 2 is a graph showing the metabolic activity (CCK-8) of devices comparing several cell scaffolding materials. The results presented indicate that polystyrene microspheres and PET yarn were good candidates for further investigation.
Figure 3:
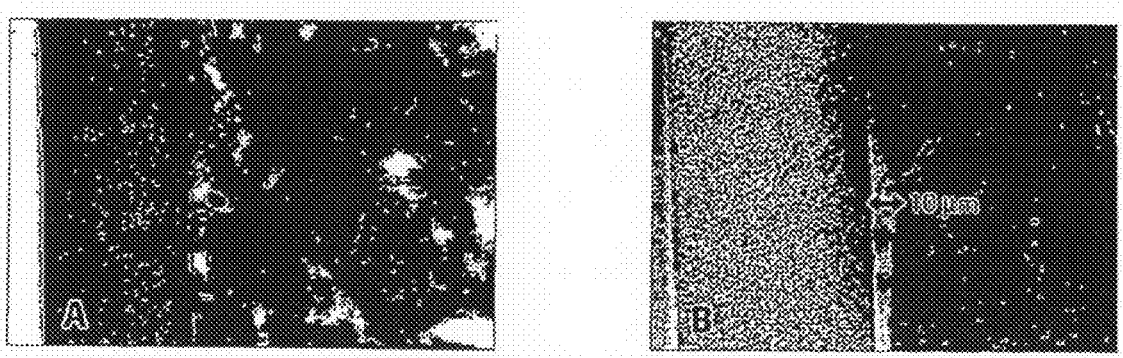
FIG. 3 is a series of photomicrographs demonstrating that both polysulfone (hydrophilic) and polyimide (hydrophobic) materials were investigated as encapsulation membranes.
Figure 4:
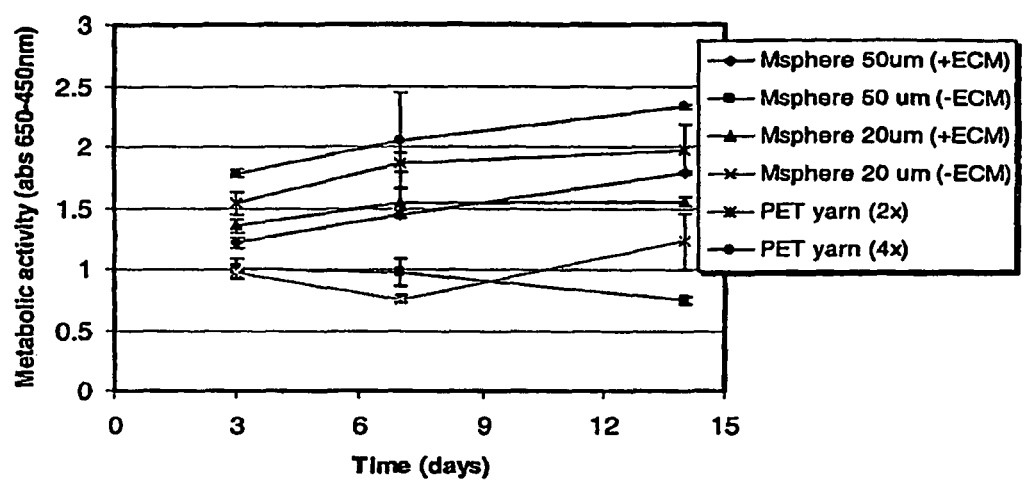
FIG. 4 is a graph showing the metabolic activity of microencapsulated devices over course of 2-weeks. These results indicate that scaffoldings coated with fibronectin promoted cell attachment to microspheres. Moreover, increasing yarn content may also benefit cell growth and activity.
Figure 5:
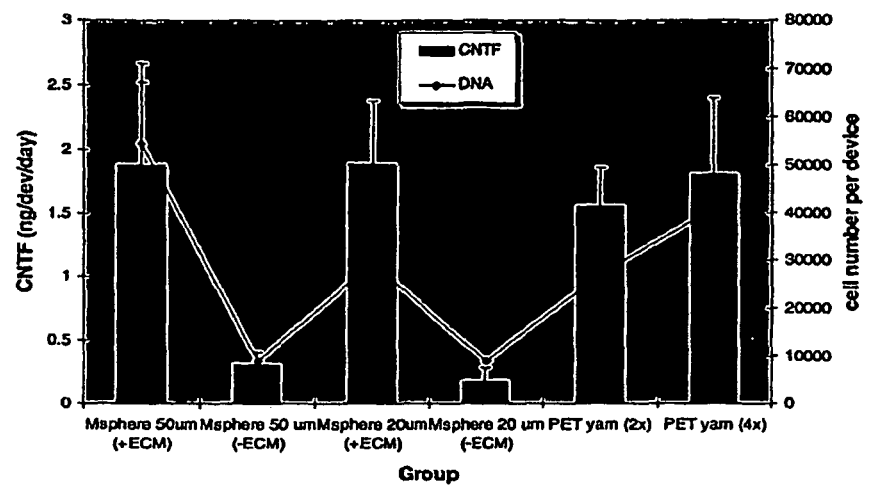
FIG. 5 is a histogram showing CNTF production and DNA assayed cell number of cells contained within the micronized devices. These results confirmed the advantages of using fibronectin to coat microspheres and demonstrated that an increase in yarn density benefits encapsulated cell performance.
Figure 6:
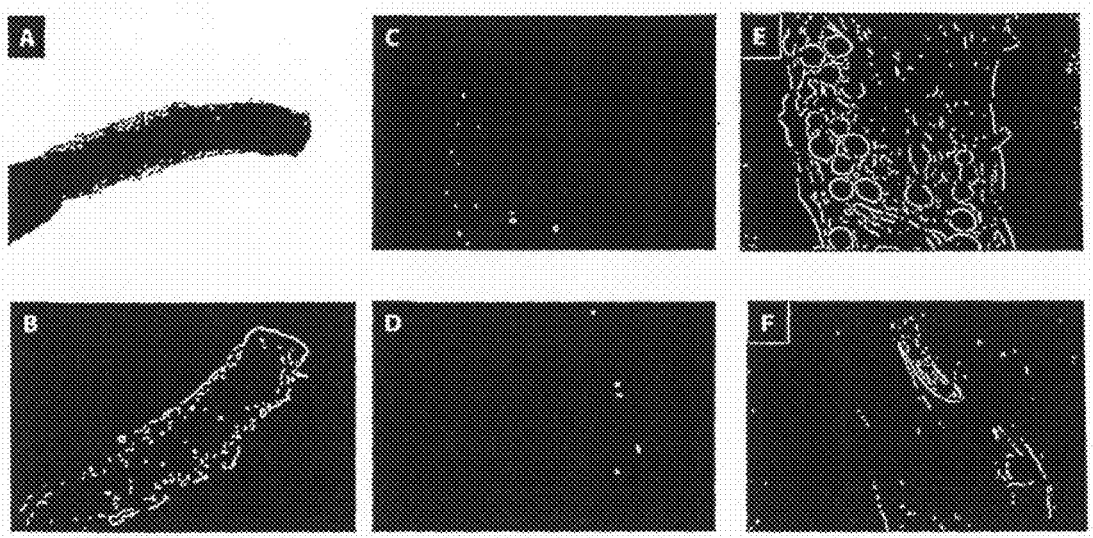
FIG. 6 is a series of photomicrographs showing the qualitative assessment of microencapsulated cell viability using polysulfone membranes and either a matrix of microspheres coated with fibronectin or a matrix of PET scaffolding. Panel A is a micrograph of an extruded cell-microsphere tissue mass following 2-weeks of encapsulation. Panel B shows the extruded cell mass stained with calcein and ethidium to visualize live and dead cells. Panels C (microspheres) and D (PET yarn) are plastic embedded sections stained with DAPI and counter stained with fluorescein 12-dUPT to visualize apoptotic cells. Few apoptotic cells were observed in either device group. Panels E (microspheres) and F (PET yarn) show hemotoxylin and eosin stained plastic sections. Cell viability and distribution were good regardless of cell matrix investigated.

As shown in FIG. 2, the use of hydrogel matrices did not allow adequate cell viability following an initial screen of micronized devices. Additionally, polyimide device groups resulted in poor viability compared to polysulfone ("PS") groups. (See FIG. 3). However, polysulfone/polyvinyl pyrrolidone membranes using either polystyrene microspheres ("PS-microsphere") coated with fibronectin or PET yarn as a cell scaffold resulted in sustained levels of protein production over the course of a one-month evaluation period. Cells encapsulated within both the PS-microsphere and PET groups of micronized devices remained healthy with no evidence of necrosis or apoptosis. (See FIGS. 4-6). In addition, a dose effect delivery of IL-10 and CNTF was achieved using micronized devices formulated with a PET yarn matrix. (See Table 1).

TABLE 1

Results of IL-10 and CNTF production in micronized devices designed using PET yarn matrix.

| Device Group | IL-10 (pg/device/24 hrs) | CNTF (pg/device/24 hrs) |
| --- | --- | --- |
| High Dose | 156 ± 32 | 2.01 ± 0.7 |
| Low Dose | 11 ± 11 | 0.3 ± 0.1 |
| t-test (95% CI) | P < 0.001 | P < 0.001 |

Clinical evaluation of micronized devices implanted into the vitreous of mice showed that these devices remained in a fixed position and avoided contact with the large rat lens. Moreover, no adverse findings were reported during the course of the one-month follow-up period. Based upon these initial experiments, it appears that manufacture and maintenance of micronized ECT devices capable of producing sustained levels of protein are possible and that these devices are well tolerated in the rodent vitreous.

As used herein, the term "individual" or "recipient" or "host" refers to a human or an animal subject.

A "biologically active molecule" ("BAM") is a substance that is capable of exerting a biologically useful effect upon the body of an individual in whom a micronized device of the present invention is implanted. As used herein a BAM is one which may exert its biological activity within the cell in which it is made or it may be expressed on the cell surface and effect the cell's interactions with other cells or biologically active molecules (e.g., a neurotransmitter receptor or cell adhesion molecule) or it may be released or secreted from the cell in which it is made and exert its effect on a separate target cell (e.g., a neurotransmitter, hormone, growth factor, soluble receptor, antibody, antibody fragment, anti-angiogenic factor, or cytokine). A BAM is any agent, such as a virus, protein, peptide, amino acid, lipid, carbohydrate, nucleic acid, nucleotide, drug, pro-drug or other substance that may have an effect on cells whether such effect is harmful, beneficial, or otherwise. BAMs that are beneficial to nervous system cells are "neurological agents", a term which encompasses any biologically or pharmaceutically active substance that may prove potentially useful for the proliferation, differentiation or functioning of CNS or eye cells or treatment of neurological or opthalmological disease or disorder. For example, the term may encompass certain neurotransmitters, neurotransmitter receptors, growth factors, growth factor receptors, soluble receptors, antibodies, antibody fragments, anti-angiogenic factors and the like, as well as enzymes used in the synthesis of these agents.

The terms "capsule" and "device" and "vehicle" are used interchangeably herein to refer to the micronized ECT devices of the invention.

Unless otherwise specified, the term "cells" means cells in any form, including but not limited to cells retained in tissue, cell clusters, and individually isolated cells.

As used herein a "biocompatible capsule" or "biocompatible device" or "biocompatible vehicle" means that the capsule or device or vehicle, upon implantation in an individual, does not elicit a detrimental host response sufficient to result in the rejection of the capsule or to render it inoperable, for example through degradation.

As used herein an "immunoisolatory capsule" or "immunoisolatory device" or "immunoisolatory vehicle" means that the capsule upon implantation into an individual, minimizes the deleterious effects of the host's immune system on the cells within its core.

As used herein "long-term, stable expression of a biologically active molecule" means the continued production of a biologically active molecule at a level sufficient to maintain its useful biological activity for periods greater than one month, preferably greater than three months and most preferably greater than six months. Implants of the micronized devices and the contents thereof are able to retain functionality for greater than three months in vivo and in many cases for longer than a year. The first generation ECT devices have been shown to be able to retain functionality for at least 18 months. Accordingly, it is believed that the micronized devices of the instant invention will be able to maintain viability and production for equal or longer periods of time in vivo. In addition, the devices of the current invention may be prepared of sufficient size to deliver an entire therapeutic dose of a substance from a single or just a few (i.e., less than approximately 50) implanted and easily retrievable devices.

The "semi-permeable" nature of the jacket membrane surrounding the core permits molecules produced by the cells (e.g., metabolites, nutrients and/or therapeutic substances) to diffuse from the device into the surrounding host eye tissue, but is sufficiently impermeable to protect the cells in the core from detrimental immunological attack by the host.

The core of the immunoisolatory vehicle is constructed to provide a suitable local environment for the continued vitality and function of particular cells isolated therein. The core may contain a scaffold or a liquid medium sufficient to maintain the cells.

The core of the micronized devices of the invention can function as a reservoir for growth factors (e.g., prolactin, or insulin-like growth factor 2), growth regulatory substances such as transforming growth factor β (TGF-β) or the retinoblastoma gene protein or nutrient-transport enhancers (e.g., perfluorocarbons, which can enhance the concentration of dissolved oxygen in the core). Certain of these substances are also appropriate for inclusion in liquid media.

In addition, the instant devices can also be used as a reservoir for the controlled delivery of needed drugs or biotherapeutics. In such cases, the core contains a high concentration of the selected drug or biotherapeutic (alone or in combination with cells or tissues). In addition, satellite vehicles containing substances which prepare or create a hospitable environment in the area of the body in which a micronized device according to the invention is implanted can also be implanted into a recipient. In such instances, the devices containing immunoisolated cells are implanted in the region along with satellite vehicles releasing controlled amounts of, for example, a substance which down-modulates or inhibits an inflammatory response from the recipient (e.g., anti-inflammatory steroids), or a substance which stimulates the ingrowth of capillary beds (e.g., an angiogenic factor).

The surrounding or peripheral region (jacket) which surrounds the core of the instant micronized devices can be permselective, biocompatible, and/or immunoisolatory. It is produced in such a manner that it is free of isolated cells, and completely surrounds (i.e., isolates) the core, thereby preventing contact between any cells in the core and the recipient's body. Biocompatible semi-permeable hollow fiber membranes, and methods of making them are disclosed in U.S. Pat. Nos. 5,284,761 and 5,158,881 (see also, WO 95/05452), each of which incorporated herein by reference in its entirety. For example, the capsule jacket can be formed from a polyether sulfone hollow fiber, such as those described in U.S. Pat. Nos. 4,976,859 and 4,968,733, and 5,762,798, each incorporated herein by reference.

To be permselective, the jacket is formed in such a manner that it has a molecular weight cut off ("MWCO") range appropriate both to the type and extent of immunological reaction anticipated to be encountered after the device is implanted and to the molecular size of the largest substance whose passage into and out of the device into the eye is desirable. The type and extent of immunological attacks which may be mounted by the recipient following implantation of the device depend in part upon the type(s) of moiety isolated within it and in part upon the identity of the recipient (i.e., how closely the recipient is genetically related to the source of the BAM). When the implanted tissue or cells are allogeneic to the recipient, immunological rejection may proceed largely through cell-mediated attack by the recipient's immune cells against the implanted cells. When the tissue or cells are xenogeneic to the recipient, molecular attack through assembly of the recipient's cytolytic complement attack complex may predominate, as well as the antibody interaction with complement.

The jacket allows passage into the eye of substances up to a predetermined size, but prevents the passage of larger substances. More specifically, the surrounding or peripheral region is produced in such a manner that it has pores or voids of a predetermined range of sizes, and, as a result, the device is permselective. The MWCO of the surrounding jacket must be sufficiently low to prevent access of the substances required to carry out immunological attacks to the core, yet sufficiently high to allow delivery of the BAM to the recipient's eye. Preferably, the MWCO of the biocompatible jacket of the micronized devices of the instant invention is from about 1 kD to about 150 kD.

As used herein with respect to the jacket of the device, the term "biocompatible" refers collectively to both the device and its contents. Specifically, it refers to the capability of the implanted intact micronized device and its contents to avoid the detrimental effects of the body's various protective systems and to remain functional for a significant period of time. As used herein, the term "protective systems" refers to the types of immunological attack which can be mounted by the immune system of an individual in whom the instant vehicle is implanted, and to other rejection mechanisms, such as the fibrotic response, foreign body response and other types of inflammatory response which can be induced by the presence of a foreign object in the individuals' body, In addition to the avoidance of protective responses from the immune system or foreign body fibrotic response, the term "biocompatible", as used herein, also implies that no specific undesirable cytotoxic or systemic effects are caused by the vehicle and its contents such as those that would interfere with the desired functioning of the vehicle or its contents.

The external surface of the micronized device can be selected or designed in such a manner that it is particularly suitable for implantation. at a selected site. For example, the external surface can be smooth, stippled or rough, depending on whether attachment by cells of the surrounding tissue is desirable. The shape or configuration can also be selected or designed to be particularly appropriate for the implantation site chosen.

The biocompatibility of the surrounding or peripheral region (jacket) of the micronized device is produced by a combination of factors. Important for biocompatibility and continued functionality are device morphology, hydrophobicity and the absence of undesirable substances either on the surface of, or leachable from, the device itself. Thus, brush surfaces, folds, interlayers or other shapes or structures eliciting a foreign body response are avoided. Moreover, the device-forming materials are sufficiently pure to insure that unwanted substances do not leach out from the device materials themselves. Additionally, following device preparation, the treatment of the external surface of the device with fluids or materials (e.g. serum) which may adhere to or be absorbed by the device and subsequently impair device biocompatibility is avoided.

First, the materials used to form the device jacket are substances selected based upon their ability to be compatible with, and accepted by, the tissues of the recipient of the implanted micronized device. Substances are used which are not harmful to the recipient or to the isolated cells. Preferred substances include polymer materials, i.e., thermoplastic polymers. Particularly preferred thermoplastic polymer substances are those which are modestly hydrophobic, i.e. those having a solubility parameter as defined in Brandrup J., et al. Polymer Handbook 3rd Ed., John Wiley & Sons, NY (1989), between 8 and 15, or more preferably, between 9 and 14 $(\text{Joules/m}^3)^{1/2}$. The polymer substances are chosen to have a solubility parameter low enough so that they are soluble in organic solvents and still high enough so that they will partition to form a proper membrane. Such polymer substances should be substantially free of labile nucleophilic moieties and be highly resistant to oxidants and enzymes even in the absence of stabilizing agents. The period of residence in vivo which is contemplated for the particular vehicle must also be considered: substances must be chosen which are adequately stable when exposed to physiological conditions and stresses. Many thermoplastics are known which are sufficiently stable, even for extended periods of residence in vivo, such as periods in excess of one or two years. Examples of stable materials include, but are not limited to, polyacrilonitrile/polyvinylchloride ("PAN/PVC" or "thermoplastic"), polyacrylonitrile, polymethylmethacrylate, polyvinyldifluoride, polyolefins, polysulfones, polymide, and/or celluloses.

The choice of materials used to construct the device is determined by a number of factors as described in detail in Dionne WO 92/19195, herein incorporated by reference. Briefly, various polymers and polymer blends can be used to manufacture the capsule jacket. Polymeric membranes forming the device and the growth surfaces therein may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, poly(acrylonitrile/covinyl chloride), as well as derivatives, copolymers and mixtures thereof.

A preferred membrane casting solution comprises a either a polysulfone dissolved in the water-miscible solvent dimethylacetamide (DMACSO) or polyethersulfone dissolved in the water-miscible solvent butyrolactone. This casting solution can optionally comprise hydrophilic or hydrophobic additives which affect the permeability characteristics of the finished membrane. A preferred hydrophilic additive for the polysulfone or polyethersulfone is polyvinylpyrrolidone (PVP). Other suitable polymers comprise polyacrylonitrile (PAN), polymethylmethacrylate (PMMA), polyvinyldifluoride (PVDF), polyethylene oxide, polyolefins (e.g., polyisobutylene or polypropylene), polyacrylonitrile/polyvinyl chloride (PAN/PVC), and/or cellulose derivatives (e.g., cellulose acetate or cellulose butyrate). Compatible water-miscible solvents for these and other suitable polymers and copolymers are found in the teachings of U.S. Pat. No. 3,615,024.

Second, substances used in preparing the biocompatible jacket of the device are either free of leachable pyrogenic or otherwise harmful, irritating, or immunogenic substances or are exhaustively purified to remove such harmful substances. Thereafter, and throughout the manufacture and maintenance of the device prior to implantation, great care is taken to prevent the adulteration or contamination of the device or jacket with substances, which would adversely affect its biocompatibility.

Third, the exterior configuration of the device, including its texture, is formed in such a manner that it provides an optimal interface with the eye of the recipient after implantation. Certain device geometries have also been found to specifically elicit foreign body fibrotic responses and should be avoided. Thus, devices should not contain structures having interlayers such as brush surfaces or folds. In general, opposing vehicle surfaces or edges either from the same or adjacent vehicles should be at least 1 mm apart, preferably greater than 2 mm and most preferably greater than 5 mm. Preferred embodiments include cylinders having an outer diameter of between about 200 and 350 μm and a length between about 0.5 and 6 mm. Preferably, the cores of the micronized device of the invention have a volume of less than 0.5 μl (e.g., about 0.3 μl).

The surrounding jacket of the biocompatible micronized devices can optionally include substances which decrease or deter local inflammatory response to the implanted vehicle and/or generate or foster a suitable local environment for the implanted cells or tissues. For example antibodies to one or more mediators of the immune response could be included. Available potentially useful antibodies such as antibodies to the lymphokines tumor necrosis factor (TNF), and to interferons (IFN) can be included in the matrix precursor solution. Similarly, an anti-inflammatory steroid can be included. See Christenson, L., et al., J. Biomed. Mat. Res., 23, pp. 705-718 (1989); Christenson, L., Ph.D. thesis, Brown University, 1989, herein incorporated by reference. Alternatively, a substance which stimulates angiogenesis (ingrowth of capillary beds) can be included.

In some embodiments, the jacket of the present micronized device is immunoisolatory. That is, it protects cells in the core of the device from the immune system of the individual in whom the device is implanted. It does so (1) by preventing harmful substances of the individual's body from entering the core, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

The external jacket may be either an ultrafiltration membrane or a microporous membrane. Those skilled in the art will recognize that ultrafiltration membranes are those having a pore size range of from about 1 to about 100 nanometers while a microporous membrane has a range of between about 0.05 to about 10 microns. The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 50 or 20 to 75 microns are particularly preferred. Types of immunological attack which can be prevented or minimized by the use of the instant device include attack by macrophages, neutrophils, cellular immune responses (e.g. natural killer cells and antibody-dependent T cell-mediated cytoloysis (ADCC)), and humoral response (e.g. antibody-dependent complement mediated cytolysis).

The type and extent of immunological response by the recipient to the implanted device will be influenced by the relationship of the recipient to the isolated cells within the core. For example, if core contains syngeneic cells, these will not cause a vigorous immunological reaction, unless the recipient suffers from an autoimmunity with respect to the particular cell or tissue type within the device. Syngeneic cells or tissue are rarely available. In many cases, allogeneic or xenogeneic cells or tissue (i.e., from donors of the same species as, or from a different species than, the prospective recipient) may be available. The use of immunoisolatory devices allows the implantation of allogeneic or xenogeneic cells or tissue, without a concomitant need to immunosuppress the recipient. Use of immunoisolatory capsules also allows the'use of unmatched cells (allographs). Therefore, the instant device makes it possible to treat many more individuals than can be treated by conventional transplantation techniques.

The type and vigor of an immune response to xenografted tissue is expected to differ from the response encountered when syngeneic or allogeneic tissue is implanted into a recipient. This rejection may proceed primarily by cell-mediated, or by complement-mediated attack. The exclusion of IgG from the core of the vehicle is not the touchstone of immunoprotection, because in most cases IgG alone is insufficient to produce cytolysis of the target cells or tissues. Using immunoisolatory micronized devices, it is possible to deliver needed high molecular weight products or to provide metabolic functions pertaining to high molecular weight substances, provided that critical substances necessary to the mediation of immunological attack are excluded from the immunoisolatory capsule. These substances may comprise the complement attack complex component Clq, or they may comprise phagocytic or cytotoxic cells. Use of immunoisolatory capsules provides a protective barrier between these harmful substances and the isolated cells.

In previous devices, the core and jacket were linked via ionic bonds between oppositely charged polymers in one of two ways. For example, the devices of Rha (U.S. Pat. No. 4,744,933) were constructed of a charged inner core material and an outer jacket material of the opposite charge. Likewise, the devices of Lim and Sun (U.S. Pat. Nos. 4,352,833 and 4,409,331) included an intermediate layer of poly-L-lysine (PLL), which is positively charged, to link the negatively charged core with the negatively charged jacket material. The elimination of a PLL layer is advantageous in that PLL is believed to be fibrogenic in the host. PLL may also have unwanted growth effects for some cells. Also, the jacket of the device of the invention can be controlled for permselectivity better than those made with PLL.

The micronized devices of the present invention are distinguished from the microcapsules of Rha, Lim, and Sun (Rha, C. K. et al., U.S. Pat. No. 4,744,933; Sun, A. M., Methods in Enzymology 137, pp. 575-579 (1988)) by (1) the complete exclusion of cells from the outer layer of the device, and (2) the thickness of the outer layer of the device. Both qualities contribute to the immunoisolation of encapsulated cells in the present invention. The microcapsules of Rha were formed by ionic interaction of an ionic core solution with an ionic polymer of opposite charge. The microcapsules of Lim and Sun were formed by linking an external hydrogel jacket to the core through an intermediate layer of poly-L-lysine (PLL). In the microcapsules of Lim and Sun, the intermediate PLL layer was not sufficiently thick to guarantee that portions of the encapsulated cells would not penetrate through and beyond the layer. Cells penetrating the PLL layer are potential targets for an immune response.

Moreover, in the microcapsules of Rha, Lim, and Sun, because the chemical identity of the inner substance is either dictated by choice of outer layer, or PLL, the ability to vary growth conditions on the inside of these capsules is greatly limited. Since there are often specific growth conditions which need to be met in order to successfully encapsulate specific cell types, these capsules generally have a limited utility or require considerable experimentation to establish appropriate outer layers for a given internal substance.

Thus, the microcapsules of Rha, Lim, and Sun have a greater potential for bioincompatibility, fibrogenesis, and vehicle deterioration than the micronized devices of the present invention. A variety of biological systems are known to interact with and break down the ionic bonds required for the integrity of microcapsules. PLL evokes unfavorable tissue reactions to the capsule. Most notably, this is a fibrotic response. Thus, if there is any break in the external layer, if it is not of sufficient thickness, if the PLL layer begins to degrade, and/or if encapsulated cells are entrapped within the external layer sufficiently close to its outer surface, the microcapsule can trigger a fibrotic response. The term "fibrogenic" is used herein in reference to capsules or materials which elicit a fibrotic response in the implantation site.

In addition, the micronized devices of the present invention are also distinguished from microcapsules (see Sun, A. M., supra; Rha, U.S. Pat. No. 4,744,933) by the capacity of micronized devices to contain between $5 \times 10^2$ and $90 \times 10^3$ cells and maintain them in viable condition. In contrast, prior art microcapsules typically contain up to about 500 cells per capsule.

The devices described herein must provide, in at least one dimension, sufficiently close proximity of any isolated cells in the core to the surrounding eye tissues of the recipient in order to maintain the viability and function of the isolated cells. However, the diffusional limitations of the materials used to form the device do not in all cases solely prescribe its configurational limits. Certain additives can be used which alter or enhance the diffusional properties, or nutrient or oxygen transport properties, of the basic vehicle. For example, the internal medium of the core can be supplemented with oxygen-saturated perfluorocarbons, thus reducing the needs for immediate contact with blood-borne oxygen. This will allow isolated cells or tissues to remain viable while, for instance, a gradient of angiotensin is released from the vehicle into the surrounding tissues, stimulating ingrowth of capillaries. References and methods for use of perfluorocarbons are given by Faithful, N. S. Anaesthesia, 42, pp. 234-242 (1987) and NASA Tech Briefs MSC-21480, U.S. Govt. Printing Office, Washington, D.C. 20402, incorporated herein by reference. Alternatively for clonal cell lines such as PC12 cells, genetically engineered hemoglobin sequences may be introduced into the cell lines to produce superior oxygen storage. See NPO-17517 NASA Tech Briefs, 15, p. 54.

The thickness of the device jacket should be sufficient to prevent an immunoresponse by the patient to the presence of the devices. For that purpose, the devices preferably have a minimum thickness of 1 µm or more and are free of the cells.

Additionally, reinforcing structural elements can be incorporated into the micronized devices. These structural elements can be made in such a fashion that they are impermeable and are appropriately configured to allow tethering or suturing of the device to the eye tissues of the recipient. In certain circumstances, these elements can act to securely seal the jacket (e.g., at the ends of the cylinder), thereby completing isolation of the core materials (e.g., a molded thermoplastic clip). In many embodiments, it is desirable that these structural elements should not occlude a significant area of the permselective jacket.

The scaffold defines the microenvironment for the encapsulated cells and keeps the cells well distributed within the core. The optimal internal scaffold for a particular device is highly dependent on the cell type to be used. In the absence of a scaffold, adherent cells aggregate to form clusters.

The filaments used to form a yarn or mesh internal scaffold are formed of any suitable biocompatible, substantially non-degradable material. (See U.S. Pat. Nos. 6,303,136 and 6,627,422, which are herein incorporated by reference). Materials useful in forming yarns or woven meshes include any biocompatible polymers that are able to be formed into fibers such as, for example, acrylic, polyester, polyethylene, polypropylene, polyacrylonitrile, polyethylene terephthalate, nylon, polyamides, polyurethanes, polybutester, or natural fibers such as cotton, silk, chitin or carbon. Any suitable thermoplastic polymer, thermoplastic elastomer, or other synthetic or natural material having fiber-forming properties may be inserted into a pre-fabricated hollow fiber membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and has a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation) to enhance cellular adhesion to the filaments.

In some embodiments, the filaments, preferably organized in anon-random unidirectional orientation, are twisted in bundles to form yarns of varying thickness and void volume. Void volume is defined as the spaces existing between filaments. The void volume in the yarn should vary between 20-95%, but is preferably between 50-95%. The preferred void space between the filaments is between 20-200 µm, sufficient to allow the scaffold to be seeded with cells along the length of the yarn, and to allow the cells to attach to the filaments. The preferred diameter of the filaments comprising the yarn is between 5-100 µm. These filaments should have sufficient mechanical strength to allow twisting into a bundle to comprise a yarn. The filament cross-sectional shape can vary, with circular, rectangular, elliptical, triangular, and star-shaped cross-section being preferred.

Alternatively, the filaments or yarns can be woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

In some embodiments, a tubular braid is constructed. The braid can be inserted into a hollow fiber membrane upon which the cells are seeded. Alternatively, the cells can be allowed to infiltrate the wall of the mesh tube to maximize the surface area available for cell attachment. When such cell infiltration occurs, the braid serves both as a cell scaffold matrix and as an inner support for the device. The increase in tensile strength for the braid-supported device is significantly higher than in alternative approaches.

The micronized device of the present invention is of a sufficient size and durability for complete retrieval after implantation. The preferred micronized devices of the present invention have a core of a preferable minimum volume of less than about 0.5 µl (e.g., about 0.3 µl).

Preferably, the micronized device has a tether that aids in maintaining device placement during implant, and aids in retrieval. Such a tether may have any suitable shape that is adapted to secure the capsule in place. For example, the suture may be a loop, a disk, or a suture. In some embodiments, the tether is shaped like an eyelet, so that suture may be used to secure the tether (and, thus, the device) to the sclera, or other suitable ocular structure. In other embodiments, the tether is continuous with the capsule at one end, and forms a pre-threaded suture needle at the other end. The tether may be constructed of a shape memory metal and/or any other suitable medical grade material known in the art.

Cells which are genetically engineered to secrete antibodies may also be included in the core. At least one additional BAM can be delivered from the micronized device to the eye. For example, the at least one additional BAM can be provided from a cellular or a noncellular source. When the at least one additional BAM is provided from a noncellular source, the additional BAM(s) may be encapsulated in, dispersed within, or attached to one or more components of the cell system. For example, the least one additional biologically active molecule can be a nucleic acid, a nucleic acid fragment, a peptide, a polypeptide, a peptidomimetic, a carbohydrate, a lipid, an organic molecule, an inorganic molecule, a therapeutic agent, or any combinations thereof. Specifically, the therapeutic agents may be an anti-angiogenic drug, a steroidal and nonsteroidal anti-inflammatory drug, an anti-mitotic drug, an anti-tumor drug, an anti-parasitic drug, an IOP reducer, a peptide drug, and any other biologically active molecule drugs approved for ophthalmologic use.

The instant invention also relates to methods for making a micronized device. Micronized devices may be formed by any suitable method known in the art. (See. e.g., U.S. Pat. Nos. 6,361,771; 5,639,275; 5,653,975; 4,892,538; 5,156,844; 5,283,138; and 5,550,050, each of which is incorporated herein by reference).

Encapsulated cell therapy is based on the concept of isolating cells from the recipient host's immune system by surrounding the cells with a semipermeable biocompatible material before implantation within the host. The invention includes a micronized device in which ARPE-19 cells are encapsulated in an immunoisolatory capsule, which, upon implantation into a recipient host, minimizes the deleterious effects of the host's immune system on the ARPE-19 cells in the core of the device. ARPE-19 cells are immunoisolated from the host by enclosing them within implantable polymeric capsules formed by a microporous membrane. This approach prevents the cell-to-cell contact between the host and implanted tissues, thereby eliminating antigen recognition through direct presentation.

The membranes used can also be tailored to control the diffusion of molecules, such as antibody and complement, based on their molecular weight. (See Lysaght et al., 56 J. Cell Biochem. 196 (1996), Colton, 14 Trends Biotechnol. 158 (1996)). Using encapsulation techniques, cells can be transplanted into a host without immune rejection, either with or without use of immunosuppressive drugs. The capsule can be made from a biocompatible material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics.

Preferably, the capsule of this invention will be similar to those described by PCT International patent applications WO 92/19195 or WO 95/05452, incorporated by reference; or U.S. Pat. Nos. 5,639,275; 5,653,975; 4,892,538; 5,156,844; 5,283,187; or 5,550,050, incorporated by reference. Components of the biocompatible material may include a surrounding semipermeable membrane and the internal cell-supporting scaffolding. The transformed cells are preferably seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation. (See U.S. Pat. No. 5,512,600, incorporated by reference). Biodegradable polymers include those comprised of polylactic acid) PLA, poly(lactic-coglycolic acid) PLGA, and poly(glycolic acid) PGA and their equivalents. Foam scaffolds have been used to provide surfaces onto which transplanted cells may adhere (PCT International patent application Ser. No. 98/05304, incorporated by reference). Woven mesh tubes have been used as vascular grafts (PCT International patent application WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. No. 4,976,859 or U.S. Pat. No. 4,968,733, incorporated by reference. An alternate surrounding semipermeable membrane material is polysulfone.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

If a device with a jacket of thermoplastic or polymer membrane is desired, the pore size range and distribution can be determined by varying the solids content of the solution of precursor material (the casting solution), the chemical composition of the water-miscible solvent, or optionally including a hydrophilic or hydrophobic additive to the casting solution, as taught by U.S. Pat. No. 3,615,024. The pore size may also be adjusted by varying the hydrophobicity of the coagulant and/or of the bath.

Typically, the casting solution will comprise a polar organic solvent containing a dissolved, water-insoluble polymer or copolymer. This polymer or copolymer precipitates upon contact with a solvent-miscible aqueous phase, forming a permselective membrane at the site of interface. The size of pores in the membrane depends upon the rate of diffusion of the aqueous phase into the solvent phase; the hydrophilic or hydrophobic additives affect pore size by altering this rate of diffusion. As the aqueous phase diffuses farther into the solvent, the remainder of the polymer or copolymer is precipitated to form a trabecular support which confers mechanical strength to the finished device.

The external surface of the device is similarly determined by the conditions under which the dissolved polymer or copolymer is precipitated (i.e., exposed to the air, which generates an open, trabecular or sponge-like outer skin, immersed in an aqueous precipitation bath, which results in a smooth permselective membrane bilayer, or exposed to air saturated with water vapor, which results in an intermediate structure).

The surface texture of the device is dependent in part on whether the extrusion nozzle is positioned above, or immersed in, the bath: if the nozzle is placed above the surface of the bath a roughened outer skin of PAN/PVC will be formed, whereas if the nozzle is immersed in the bath a smooth external surface is formed.

The surrounding or peripheral matrix or membrane can be preformed, filled with the materials which will form the core (for instance, using a syringe), and subsequently sealed in such a manner that the core materials are completely enclosed. The device can then be exposed to conditions which bring about the formation of a core matrix if a matrix precursor material is present in the core.

Any suitable method of sealing the device may be used, including the employment of polymer adhesives and/or crimping, knotting and heat sealing. These sealing techniques are known in the. art. In addition, any suitable "dry" sealing method can also be used. In such methods, a substantially non-porous fitting is provided through which the cell-containing solution is introduced. Subsequent to filling, the device is sealed. Such methods are described in, e.g., U.S. Pat. Nos. 5,653,688; 5,713,887; 5,738,673; 6,653,687; 5,932,460; and 6,123,700, which are herein incorporated by reference.

The devices of the invention can provide for the implantation of diverse cell or tissue types, including fully-differentiated, anchorage-dependent, fetal or neonatal, or transformed, anchorage-independent cells or tissue. The cells to be isolated are prepared either from a donor (i.e., primary cells or tissues, including adult, neonatal, and fetal cells or tissues) or from cells which replicate in vitro (i.e., immortalized cells or cell lines, including genetically modified cells). In all cases, a sufficient quantity of cells to produce effective levels of the needed product or to supply an effective level of the needed metabolic function is prepared, generally under sterile conditions, and maintained appropriately (e.g. in a balanced salt solution such as Hank's salts, or in a nutrient medium, such as Ham's F12) prior to isolation.

The micronized ECT devices of the invention are of a shape which tends to reduce the distance between the center of the device and the nearest portion of the jacket for purposes of permitting easy access of nutrients from the patient into the cell or of entry of the patient's proteins into the cell to be acted upon by the cell to provide a metabolic function. In that regard, a non-spherical shape, such as a cylinder, is preferred.

Four important factors that influence the number of cells or amount of tissue to be placed within the core of the device (i.e., loading density) of the instant invention are: (1) device size and geometry; (2) mitotic activity within the device; (3) viscosity requirements for core preparation and or loading; and (4) pre-implantation assay and qualification requirements.

With respect to the first of these factors, (device size and geometry), the diffusion of critical nutrients and metabolic requirements into the cells as well as diffusion of metabolites away from the cell are critical to the continued viability of the cells. In the case of RPE cells such as ARPE-19 cells, the neighboring cells are able to phagocytize the dying cells and use the debris as an energy source.

Among the metabolic requirements met by diffusion of substances into the device is the requirement for oxygen. The oxygen requirements of the specific cells must be determined for the cell of choice. See Methods and references for determination of oxygen metabolism are given in Wilson D. F. et al., J. Biol. Chem., 263, pp. 2712-2718, (1988).

With respect to the second factor (cell division), if the cells selected are expected to be actively dividing while in the device, then they will continue to divide until they fill the available space, or until phenomena such as contact inhibition limit further division. For replicating cells, the geometry and size of the device will be chosen so that complete filling of the device core will not lead to deprivation of critical nutrients due to diffusional limitations.

With respect to the third factor (viscosity of core materials) cells in densities occupying up to 70% of the device volume can be viable, but cell solutions in this concentration range would have considerable viscosity. Introduction of cells in a very viscous solution into the device could be prohibitively difficult. In general, for both two step and coextrusion strategies, cell loading densities of higher than 30% will seldom be useful, and in general optimal loading densities will be 20% and below. For example, for fragments of tissues, it is important, in order to preserve the viability of interior cells, to observe the same general guidelines as above and tissue fragments should not exceed 250 microns in diameter with the interior cells having less than 15, preferably less than 10 cells between them and the nearest diffusional surface.

Finally, with respect to the fourth factor (preimplantation and assay requirements), in many cases, a certain amount of time will be required between device preparation and implantation. For instance, it may be important to qualify the device in terms of its biological activity. Thus, in the case of mitotically active cells, preferred loading density will also consider the number of cells which must be present in order to perform the qualification assay.

In most cases, prior to implantation in vivo, it will be important to use in vitro assays to establish the efficacy of the BAM within the device. Devices can be constructed and analyzed using model systems in order to allow the determination of the efficacy of the . vehicle on a per cell or unit volume basis.

Following these guidelines for device loading and for determination of device efficacy, the actual device size for implantation will then be determined by the amount of biological activity required for the particular application. The number of devices and device size should be sufficient to produce a therapeutic effect upon implantation is determined by the amount of biological activity required for the particular application. In the case of secretory cells releasing therapeutic substances, standard dosage considerations and criteria known to the art will be used to determine the amount of secretory substance required. Factors to be considered include; the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures. Moreover, whether the recipient has a preexisting condition which can interfere with the efficacy of the implant must also be considered. Devices of the instant invention can easily be manufactured which contain many thousands of cells (e.g., between about $5 \times 10^2$ and about $90 \times 10^3$ cells).

The treatment of many conditions according to the methods described herein will require only one or at most less than 50 implanted micronized devices per eye to supply an appropriate therapeutic dose. Therapeutic dosages may be between about 0.1 pg and 1000 ng per eye per patient per day (e.g., between 0.1 pg and 500 ng per eye per patient per day; between 0.1 pg and 250 ng, between 0.1 pg and 100 ng, between 0.1 pg and 50 ng, between 0.1 pg and 25 ng, between 0.1 pg and 10 ng, or between 0.1 pg and 5 ng per eye per patient per day). Each of the devices of the present invention is capable of storing between about 1,000 and about 90,000 cells, in individual or cluster form, depending on their type.

According to the methods of this invention, other molecules may be co-delivered from the micronized devices. For example, it may be preferable to deliver a trophic factor(s) with an anti-angiogenic factor(s).

Co-delivery can be accomplished in a number of ways. First, cells may be transfected with separate constructs containing the genes encoding the described molecules. Second, cells may be transfected with a single construct containing two or more genes and the necessary control elements. Third, two or more separately engineered cell lines can be either co-encapsulated or more than one device can be implanted at the site of interest.

Multiple gene expression from a single transcript over expression from multiple transcription units can be employed. See, e.g., Macejak, Nature, 353, pp. 90-94 (1991); WO 94/24870; Mountford and Smith, Trends Genet., 11, pp. 179-84 (1995); Dirks et al., Gene, 128, pp. 247-49 (1993); Martinez-Salas et al., J. Virology, 67, pp. 3748-55 (1993) and Mountford et al., Proc. Natl. Acad. Sci. USA, 91, pp. 4303-07 (1994).

For some indications, it may be preferable to deliver BAMs to two different sites in the eye concurrently. For example, it may be desirable to deliver a neurotrophic factor to the vitreous to supply the neural retina (ganglion cells to the RPE) and to deliver an anti-angiogenic factor via the sub-Tenon's space to supply the choroidal vasculature.

Additionally, another embodiment in this invention involves the co-delivery of a BAM from a noncellular source or mixture of a BAM from a noncellular source and excipient to a region of the eye wherein the BAM from a noncellular source is encapsulated, dispersed, or attached to device components including, but not limited to: (a) sealant; (b) scaffold; (c) jacket membrane; (d) tether anchor; and/or (e) core media. In this embodiment, co-delivery of the BAM from a noncellular source may occur from the same device as the BAM from the cellular source. Alternatively, two or more encapsulated cell systems can be used. The BAM from a noncellular source can include therapeutic agents such as steroidal and non-steroidal anti-inflammatory drugs, anti-mitotic drugs, anti-tumor drugs, and-parasitic drugs, IOP reducers, peptide drugs, and other biologically active molecules approved for ophthalmologic use. Suitable excipients include, but are not limited to, any non-degradable or biodegradable polymers, hydrogels, solubility enhancers, hydrophobic molecules, proteins, salts, or other complexing agents approved for formulations.

Non-cellular dosages can be varied by any suitable method known in the art such as varying the concentration of the therapeutic agent, and/or the number of devices per eye, and/or modifying the composition of the encapsulating excipient. Cellular dosage can be varied by changing (1) the number of cells per device, (2) the number of devices per eye, or (3) the level of BAM production per cell. Cellular production can be varied by changing, for example, the copy number of the gene for the BAM in the transduced cell, or the efficiency of the promoter driving expression of the BAM. Suitable dosages from non-cellular sources may range from about 1 pg to about 1000 ng per day.

This invention also contemplates use of different cell types during the course of the treatment regime. For example, a patient may be implanted with a capsule device containing a first cell type. If after time, the patient develops an immune response to that cell type, the capsule can be retrieved, or explanted, and a second capsule can be implanted containing a second cell type. In this manner, continuous provision of the therapeutic molecule is possible, even if the patient develops an immune response to one of the encapsulated cell types.

The methods and devices of the instant invention are useful to deliver a wide range of cellular products, including high molecular weight products, to an individual in need of them, and/or to provide needed metabolic functions to an individual, such as the removal of harmful substances. Products which can be delivered using the instant devices include a wide variety of BAMs normally secreted by various organs or tissues. Alternatively, the encapsulated cells can be genetically engineered to secrete one or more BAMs.

Many cellular products which are difficult to provide using primary donor tissues can be provided using immortalized cells or cell lines. Immortalized cells are those which are capable of indefinite replication but which exhibit contact inhibition upon confluence and are not tumorigenic. An example of an immortalized cell line is the rat pheochromocytoma cell line PC12. Transformed cells or cell lines can be used in a similar manner. Transformed cells are unlike merely immortalized cells in that they do not exhibit contact inhibition upon confluence, and form tumors when implanted into an allogeneic host. Immortalization can allow the use of rare or notoriously fragile cell or tissue types for the long-term delivery of a chosen product or metabolic function. Suitable techniques for the immortalization of cells are described in Land H. et al., Nature 304, pp. 596-602 (1983) and Cepko, C. L., Neuron 1, pp. 345-353 (1988). Candidate cell lines include, for example, genetically engineered beta-cell lines which secrete insulin such as NIT cells (see Hamaguchi, K., et al., Diabetes 40, p. 842 (1991)), RIN cells (see Chick, W. L., et al., Proc. Natl. Acad. Sci. USA, 74, pp. 628-632 (1977)), ATT cells (see Hughes, S. D., et al, Proc. Natl. Acad. Sci. USA, 89, pp. 688-692 (1992)), CHO cells (see Matsumoto, M., et al, 1990, Proc. Natl. Acad. Sci. USA, 87, pp. 9133-9137 (1990)), beta-TC-3 cells (see Tal, M., et al, 1992, Mol. Cell Biol., 12, pp. 422-432 (1992)), and ARPE-19 cells. Additionally, recombinant cells or cell lines can be engineered to provide novel products or functions and combinations thereof, using a wide variety of techniques well known to those of ordinary skill in the art.

The genes encoding numerous biologically active molecules have been cloned and their nucleotide sequences published. Many of those genes are publicly available from depositories such as the American Type Culture Collection (ATCC) or various commercial sources. Genes encoding the biologically active molecules useful in this invention that are not publicly available may be obtained using standard recombinant DNA methods such as PCR amplification, genomic and cDNA library screening with oligonucleotide probes. Any of the known genes coding for biologically active molecules may be employed in the methods of this invention. See, e.g., U.S. Pat. No. 5,049,493; Gage et al., U.S. Pat. No. 5,082,670; and Genentech U.S. Pat. No. 5,167,762.

A gene of interest (i.e., a gene that encodes a suitable biologically active molecule) can be inserted into a cloning site of a suitable expression vector by using standard techniques. It will be appreciated that more than one gene may be inserted into a suitable expression vector. These techniques are well known to those skilled in the art.

The expression vector containing the gene of interest may then be used to transfect the cell line to be used in the methods of this invention. Standard transfection techniques such as calcium phosphate co-precipitation, DEAE-dextran transfection or electroporation may be utilized. Commercially available mammalian transfection kits may be purchased from e.g., Stratagene.

A wide variety of host/expression vector combinations may be used to express the gene encoding the biologically active molecule of interest. Long-term, stable in vivo expression is achieved using expression vectors (i.e., recombinant DNA molecules) in which the gene encoding the biologically active molecule is operatively linked to a promoter that is not subject to down regulation upon implantation in vivo in a mammalian host. Accordingly, such expression vectors would typically not contain a retroviral promoter. Suitable promoters include, for example, the early and late promoters of SV40 or adenovirus and other known non-retroviral promoters capable of controlling gene expression.

Useful expression vectors, for example, may consist of segments of chromosomal, non-chromosomal and synthetic DNA sequences, such as various known derivatives of SV40 and known bacterial plasmids, e.g., pUC, pBlue Script plasmids from E. coli including pBR322, pCR1, pMB9, pUC, pBlue Script™ and their derivatives. Expression vectors containing the geneticin (G418) or hygromycin drug selection genes (See Southern, P. J. (1981), In vitro, 18, p. 315, Southern, P. J. and Berg, P. (1982), J. Mol. Appl. Genet., 1, p. 327) are also useful in practicing this invention. These vectors can employ a variety of different enhancer/promoter regions to drive the expression of both a biologic gene of interest (e.g., NGF) and/or a gene conferring resistance to selection with toxin such as G418 or hygromycin B. The G418 resistance gene codes for aminoglycoside phosphotransferase (APH) which enzymatically inactivates G418 (100-500 µg/µl) added to the culture medium. Only those cells expressing the APH gene will survive drug selection usually resulting in the expression of the second biologic gene as well. The hygromycin B phosphotransferase (HPH) gene codes for an enzyme which specifically modifies hygromycin toxin and inactivates it. Genes cotransfected with or contained on the same plasmid as the hygromycin B phosphotransferase gene will be preferentially expressed in the presence of hygromycin B at 50-200 µg/ml concentrations.

A variety of different mammalian promoters can be employed to direct the expression of the genes for G418 and hygromycin B and/or the BAM gene of interest. These promoters include, but are not limited to, the promoters of hDBH (human dopamine beta hydoxylase) (see Mercer et al., Neuron, 7, pp. 703-716, (1991)), hTH (human tyrosine hydroxylase) (see Kaneda, et al., Neuron, 6, pp. 583-594, (1991)), hPNMT (human phenylethanaolamine N-methyltransferase) (see Baetge et al., pNAS, 85, pp. 3648-3652, (1988)), mGFAP (mouse glial fibrillary acidic protein) (see Besnard et al., J. Biol. Chem., 266, pp. 18877-18883, (1991)), myelin basic protein (MBP), mNF-L (mouse neurofilament-light subunit) (see Nakahira et al., J. Biol. Chem., 265, pp. 19786-19791, (1990)), hPo (human $P_0$, the promoter for the gene encoding the major myelin glycoprotein in the peripheral nervous system) (see Lemke et al., Neuron, 1, pp. 73-83, (1988)), mMT, rNSE (rat neuron-specific enolase) (see Sakimura, et al., Gene, 60, pp. 103-113, 1987), and the like.

Examples of expression vectors that can be employed include, but are not limited to, the commercially available pRC/CMV, pRC/RSV, and pCDNA1NEO (InVitrogen). The viral promoter regions directing the transcription of the drug selection and BAM genes of interest are replaced with one of the above promoter sequences that are not subject to the down regulation experienced by viral promoters within the CNS. For example, the GFAP promoter would be employed for the transfection of astrocytes and astrocyte cell lines, the TH promoter would be used in PC12 cells, or the MBP promoter would be used in oligodendrocytes.

In some embodiments, the pNUT expression vector is used. In addition, the pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

Suitable BAMs for use in the micronized devices of the invention include, but are not limited to, antiangiogenic factors, anti-inflammatory factors, neurotrophic factors, growth factors, trophic factors, antibodies and antibody fragments, neurotransmitters, hormones, cytokines, or lymphokines. Specifically, the BAMs may be TGFβ, GDNF, NGF, CNTF, bFGF, aFGF, IL-1β, IFN-β, IFN-α, BDNF, LIF, NT-4, NTN, NT4/5, CT-1, LEDGF, Neublastin, Axokine, IL-23, RdCVF, IL-10, Alpha INF, IL-1Rα, and Remicade. Exemplary antiangiogenic factors include, but are not limited to vasculostatin, angiostatin, endostatin, anti-integrins, vascular endothelial growth factor inhibitors (VEGF-inhibitors), platelet factor 4, heparinase, bFGF-binding molecules, the VEGF receptor Flt, the VEGF receptor Flk, Lucentis, VEGF Trap, TekΔ/Fc (ang1/ang2 inhibitor), 2xCon4 (C), soluble VEGF Receptors, and PEDF.

Other products which can be delivered through use of the instant micronized device include trophic factors such as erythropoietin, growth hormone, Substance P, and neurotensin. This invention is useful for treating individuals suffering from acute and/or chronic pain, by delivery of an analgesic or pain reducing substance to the individual. Such pain reducing substances include enkephalins, catecholamines and other opioid peptides. Such compounds may be secreted by, e.g., adrenal chromaffin cells. Another family of products suited to delivery by the instant vehicle comprises biological response modifiers, including lymphokines and cytokines. Antibodies from antibody secreting cells may also be delivered. Specific antibodies which may be useful include those towards tumor specific antigens. The release of antibodies may also be useful in decreasing circulating levels of compounds such as hormones or growth factors. These products are useful in the treatment of a wide variety of diseases, inflammatory conditions or disorders, and degenerative disorders of the eye.

Modified, truncated and/or mutein forms of the above-mentioned molecules are also contemplated. Further, active fragments of these growth factors (i.e., those fragments of growth factors having biological activity sufficient to achieve a therapeutic effect) are also contemplated. Also contemplated are growth factor molecules modified by attachment of one or more polyethylene glycol (PEG) or other repeating polymeric moieties. Combinations of these proteins and polycistronic versions thereof are also contemplated.

The choice of cells depends upon the intended application. The cells can be chosen for their secretion of hormones, cytokines, growth factors, trophic factors, angiogenesis factors, antibodies, blood coagulation factors, lymphokines, enzymes, and other therapeutic agents or agonists, precursors, active analogs, or active fragments thereof.

A wide variety of cells may be used in this invention. These include well known, publicly available immortalized cell lines as well as primary cell cultures. Examples of publicly available cell lines suitable for the practice of this invention include, baby hamster kidney (BHK), Chinese hamster ovary (CHO), mouse fibroblast (L-M), NIH Swiss mouse embryo (NIH/3T3), African green monkey cell lines (including COS-a, COS-7, BSC-1, BSC-40, BMT-10 and Vero), rat adrenal pheochromocytoma (PC12), rat glial tumor (C6), ARPE-19 cells, and the like. Primary cells that may be used according to the present invention include, bFGF-responsive neural progenitor-stem cells derived from the CNS of mammals (Richards et al., Proc. Natl. Acad. Sci. USA 89, pp. 8591-8595 (1992); Ray et al., Proc. Natl. Acad. Sci. USA, 90, pp. 3602-3606 (1993)), primary fibroblasts, Schwann cells, astrocytes, β-TC cells, Hep-G2 cells, AT T20 cells, oligodendrocytes and their precursors, myoblasts, adrenal chromaffin cells, and the like.

The choice of cell depends upon the intended application. The encapsulated cells may be chosen for secretion of a particular BAM. Cells can also be employed which synthesize and secrete agonists, analogs, derivatives or fragments of BAMs, which are active.

To be a platform cell line for an encapsulated cell based delivery system, the cell line should have as many of the following characteristics as possible: (1) the cells should be hardy under stringent conditions (the encapsulated cells should be functional in the avascular tissue cavities such as in the central nervous system or the eye, especially in the intraocular environment); (2) the cells should be able to be genetically modified (the desired therapeutic factors needed to be engineered into the cells); (3) the cells should have a relatively long life span (the cells should produce sufficient progenies to be banked, characterized, engineered, safety tested and clinical lot manufactured); (4) the cells should preferably be of human origin (which increases compatibility between the encapsulated cells and the host); (5) the cells should exhibit greater than 80% viability for a period of more than one month in vivo in device (which ensures long-term delivery); (6) the encapsulated cells should deliver an efficacious quantity of a useful biological product (which ensures effectiveness of the treatment); (7) the cells should have a low level of host immune reaction (which ensures the longevity of the graft); and (8) the cells should be nontumorigenic (to provide added safety to the host, in case of device leakage).

The ARPE-19 cell line (see Dunn et al., 62 Exp. Eye Res. 155-69 (1996), Dunn et al., 39 Invest. Ophthalmol. Vis. Sci. 2744-9 (1998), Finnemann et al., 94 Proc. Natl. Acad. Sci. USA 12932-7 (1997), Handa et al., 66 Exp. Eye. 411-9 (1998), Holtkamp et al., 112 Clin. Exp. Immunol. 34-43 (1998), Maidji et al., 70 J. Virol. 8402-10 (1996); U.S. Pat. No. 6,361,771) demonstrates all of the characteristics of a successful platform cell for an encapsulated cell-based delivery system. The ARPE-19 cell line is available from the American Type Culture Collection (ATCC Number CRL-2302). ARPE-19 cells are normal retinal pigmented epithelial (RPE) cells and express the retinal pigmentary epithelial cell-specific markers CRALBP and RPE-65. ARPE-19 cells form stable monolayers, which exhibit morphological and functional polarity.

When the micronized devices of the invention are used, preferably between $10^2$ and $10^8$ ARPE-19 cells, most preferably $5 \times 10^2$ to $90 \times 10^3$ ARPE-19 cells are encapsulated in each device. Dosage may be controlled by implanting a fewer or greater number of capsules, . preferably between 1 and 50 capsules per patient. The devices described herein are capable of delivering between about 0.1 pg and 1000 ng of the desired BAM per eye per patient per day. Both the first generation ECT devices as well as the micronized devices of the instant invention have been shown to provide the same level of protein to the eye.

Techniques and procedures for isolating cells or tissues which produce a selected product are known to those skilled in the art, or can be adapted from known procedures with no more than routine experimentation.

If the cells to be isolated are replicating cells or cell lines adapted to growth in vitro, it is particularly advantageous to generate a cell bank of these cells. A particular advantage of a cell bank is that it is a source of cells prepared from the same culture or batch of cells. That is, all cells originated from the same source of cells and have been exposed to the same conditions and stresses. Therefore, the vials can be treated as identical clones. In the transplantation context, this greatly facilitates the production of identical or replacement devices. It also allows simplified testing protocols, which assure that implanted cells are free of retroviruses and the like. It may also allow for parallel monitoring of vehicles in vivo and in vitro, thus allowing investigation of effects or factors unique to residence in vivo.

In all cases, it is important that the cells or tissue contained in the device are not contaminated or adulterated.

The newly-formed micronized devices obtained by any of the methods described herein can be maintained under sterile conditions in a non-pyrogenic, serum-free defined nutrient medium or balanced salt solution, at about 37° C., prior to implantation. Lower temperatures (20° C.-37° C.) may be optimal for certain cell types and/or culturing conditions. Other holding temperatures and medium compositions consistent with good cell viability may also be used. Alternatively, the device can be cryopreserved in liquid nitrogen, if a cryoprotective agent such as glycerin has been incorporated into the matrix. (See Rajotte, R. V. et al. Transplantation Proceedings, 21, pp. 2638-2640 (1989)). In such a case, the device is thawed before use and equilibrated under sterile conditions as described above.

The methods and devices of this invention are intended for use in a mammalian host, recipient, subject or individual, preferably a primate, most preferably a human. A number of different implantation sites are contemplated for the devices and methods of this invention. Suitable implantation sites include, but are not limited to, the aqueous and vitreous humors of the eye, the periocular space, the anterior chamber, and/or the Subtenon's capsule.

The invention provides methods of treating ophthalmic disorders by implanting the micronized devices of the invention into an eye of the patient. For example, the ophthalmic disorder may be a retinal degeneration disease. Exemplary retinal degeneration diseases include, but are not limited to, retinopathy of prematurity, glaucoma, cataract formation, retinoblastoma, retinal ischemia, uveitis, retinitis pigmentosa, forms of wet and dry age-related macular degeneration, diabetic retinopathy, and choroideremia. Other ophthalmic disorders that may be treated using the micronized devices of the present invention include, but are not limited to, proliferative retinopathies, retinal vascular diseases, vascular anomalies, age-related macular degeneration and other acquired disorders (including but not limited to dry age-related macular degeneration, exudative age-related macular degeneration, and myopic degeneration), endophthalmitis, infectious diseases, inflammatory but non-infectious diseases, AIDS-related disorders, ocular ischemia syndrome, pregnancy-related disorders, peripheral retinal degenerations, retinal degenerations, toxic retinopathies, retinal tumors, choroidal tumors, choroidal disorders, vitreous disorders, retinal detachment and proliferative vitreoretinopathy, non-penetrating trauma, penetrating trauma, post-cataract complications, and inflammatory optic neuropathies.

The devices of the present invention may also be useful for the treatment of ocular neovascularization, a condition associated with many ocular diseases and disorders. For example, retinal ischemia-associated ocular neovascularization is a major cause of blindness in diabetes and many other diseases. The present invention may also be used to treat ocular symptoms resulting from diseases or conditions that have both ocular and non-ocular symptoms. Some examples include cytomegalovirus retinitis in AIDS and other conditions and vitreous disorders, hypertensive changes in the retina as a result of pregnancy, and ocular effects of various infectious diseases such as tuberculosis, syphilis, Lyme disease, parasitic disease, toxocara canis, ophthalmonyiasis, cyst cercosis and fungal infections. Likewise, the invention may also be used to treat conditions relating to other intraocular neovascularization-based diseases. Corneal neovascularization is a. major problem because it interferes with vision and predisposes patients to corneal graft failure. A majority of severe visual loss is associated with disorders which result in ocular neovascularization. For example, neovascularization occurs in diseases such as diabetic retinopathy, central retinal vein occlusion and possibly age-related macular degeneration.

The micronized devices and techniques of this invention provide several advantages over other delivery routes. For example, BAMs can be delivered to the eye directly, which reduce or minimize unwanted peripheral side effects. Moreover, very small doses of BAMs (picogram or low nanogram quantities rather than milligrams) compared with topical applications can be delivered, thereby also potentially lessening side effects. Likewise, because viable cells continuously produce newly synthesized BAMs, these techniques should be superior to injection delivery of drugs,. where the BAM dose fluctuates greatly between injections and the BAM is continuously degraded but not continuously replenished.

Living cells can be encapsulated in the micronized device of the invention and surgically inserted (under retrobulbar anesthesia) into the vitreous of the eye. Preferably, the micronized device is tethered to the sclera to aid in removal. The micronized device can remain in the vitreous as long as necessary to achieve the desired prophylaxis or therapy. Such therapies for example include promotion of neuron or photoreceptor survival or repair, or inhibition and/or reversal of retinal or choroidal neovascularization, as well as inhibition of uveal, retinal and optic nerve inflammation.

With vitreal placement, the biologically active molecule, preferably a trophic factor, may be delivered to the retina or the RPE. In addition, retinal neovascularization may be best treated by delivering an anti-angiogenic factor to the vitreous.

In other embodiments, cell-loaded devices are implanted periocularly, within or beneath the space known as Tenon's capsule. This embodiment is less invasive than implantation into the vitreous as complications such as vitreal hemorrhage and/or retinal detachment are potentially eliminated. This route of administration also permits delivery of BAMs (e.g., trophic factors and the like) to the RPE or the retina. This embodiment is especially preferred for treating choroidal neovascularization and inflammation of the optic nerve and uveal tract. In general, delivery from this implantation site will permit circulation of the desired biologically active molecule to the choroidal vasculature, retinal vasculature, and the optic nerve.

Preferred embodiments include, but are not limited to, periocular delivery (implanting beneath Tenon's capsule) of anti-angiogenic molecules, anti-inflammatory molecules (such as cytokines and hormones), and neurotrophic factors to the choroidal vasculature to treat macular degeneration (choroidal neovascularization). Delivery of anti-angiogenic factors directly to the choroidal vasculature (periocularly) or to the vitreous (intraocularly) using the devices and methods of this invention may reduce the above mentioned problems and may permit the treatment of poorly defined or occult choroidal neovascularization. It may also provide a way of reducing or preventing recurrent choroidal neovascularization via adjunctive or maintenance therapy.

Implantation of the biocompatible micronized device is performed under sterile conditions. The micronized device can be implanted using a syringe or any other method known to those skilled in the art. Generally, the device is implanted at a site in the recipient's body which will allow appropriate delivery of the secreted product or function to the recipient and of nutrients to the implanted cells or tissue, and will also allow access to the device for retrieval and/or replacement. A number of different implantation sites are contemplated. These include, e.g., the aqueous humor, the vitreous humor, the sub-Tenon's capsule, the periocular space, and the anterior chamber. Preferably, for implant sites that are not immunologically privileged, such as periocular sites, and other areas outside the anterior chamber (aqueous) and the posterior chamber (vitreous), the capsules are immunoisolatory. It is preferable to verify that the cells immobilized within the micronized device function properly both before and after implantation; assays or diagnostic tests well known in the art can be used for these purposes. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them.

The invention will be further described in the following examples, which do not limit the scope of the invention described in the claims.

EXAMPLES

Example 1

Comparison of "First Generation" and Micronized ECT Devices

Materials and Methods

Figure 7:
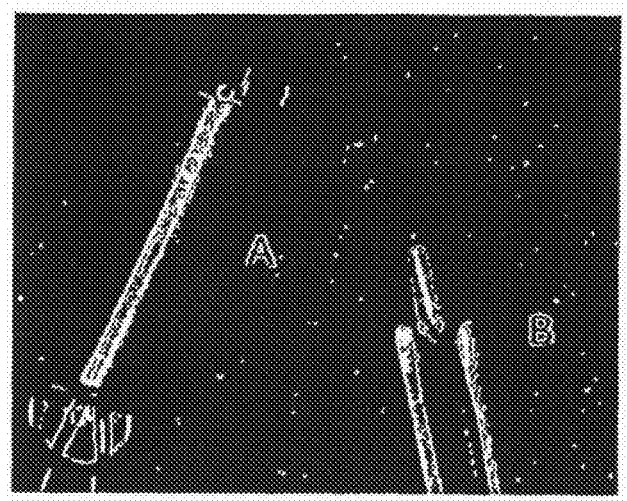
FIG. 7 is a photograph comparing the size of a first generation ECT device (1 mm×6 mm) and a micronized ECT device (0.2 mm×1 mm).

ECT devices were fabricated to allow intravitreal implantation into the eye. The first generation devices totaled 600 μl in displaced volume (1.1 mm diameter, 6 mm length). Micronized ECT devices were fabricated with a total displacement volume of 0.05 μl (200 mm diameter, 1 mm length). A comparison of the size differences between the first generation and micronized ECT devices is provided in FIG. 7. Encapsulated cell lines used in these studies were genetically modified to secrete either ciliary neurotrophic factor (CNTF) or interleukin-10 (IL-10). Devices were designed to produce a high and a low dose delivery for both CNTF and IL-10. Implant periods ranged from 2 weeks to 18 months in the rabbit model and were 2 weeks in the rat model. Protein delivery levels were quantified over the course of the studies and clinical exams were conducted to assess ocular irritation and surgical wound healing.

Results

CNTF Delivery

Figure 8:
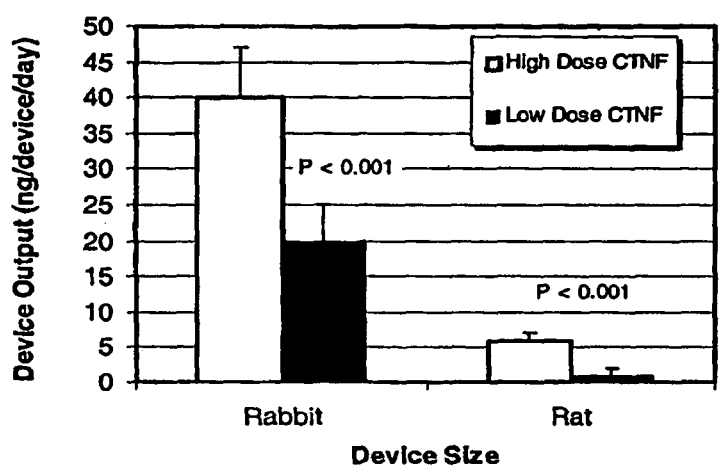
FIG. 8 is a graph showing the pre-implant dose delivery of CNTF from the first generation and the micronized ECT devices.

Dose delivery was achieved using both first generation and micronized ECT devices in both the rabbit and rat animal models. Pre-implant dose separation is shown for both size devices in FIG. 8.

Figure 9:
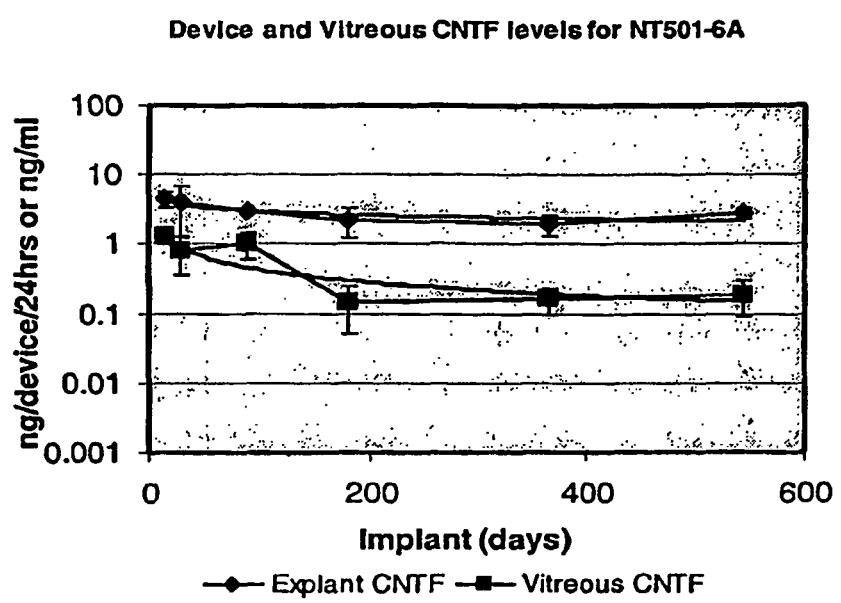
FIG. 9 is a graph showing the 18-month high dose CNTF release in rabbit vitreous (using the first generation ECT device).
Figure 10:
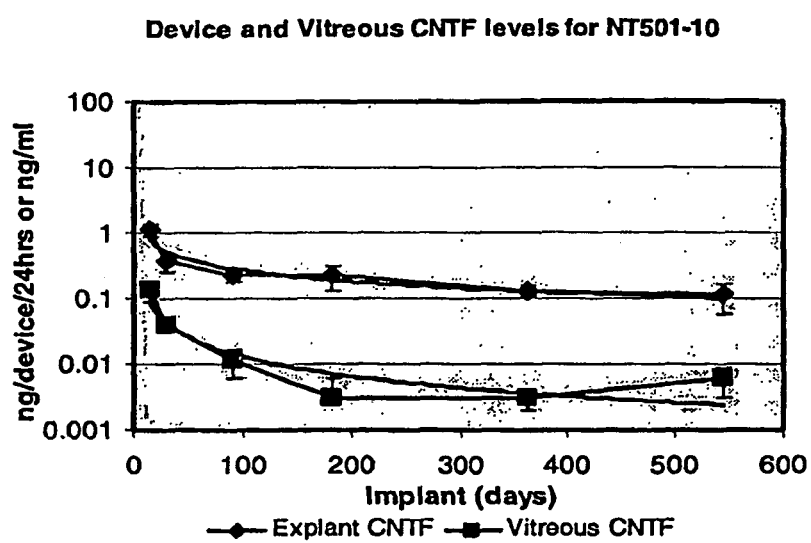
FIG. 10 is a graph showing the 18-month low dose CNTF release in rabbit vitreous (using the first generation ECT device).

Long-term implant dose delivery was achieved in the rabbit model resulting in stable delivery throughout the course of the 18 month implant. High dose CNTF delivery (ng/device/day) in the rabbit model ranged from 4.42±1.14 at 2-weeks to 2.20±1.08 at 18 months (FIG. 9). Low dose delivery (ng/device/day) ranged from 1.14±0.24 at 2 weeks to 0.11±0.06 at 18 months (FIG. 10). Vitreous CNTF levels for both high and low dose delivery were approximately 10 percent of device output and remained stable throughout the course of the study.

Figure 11:
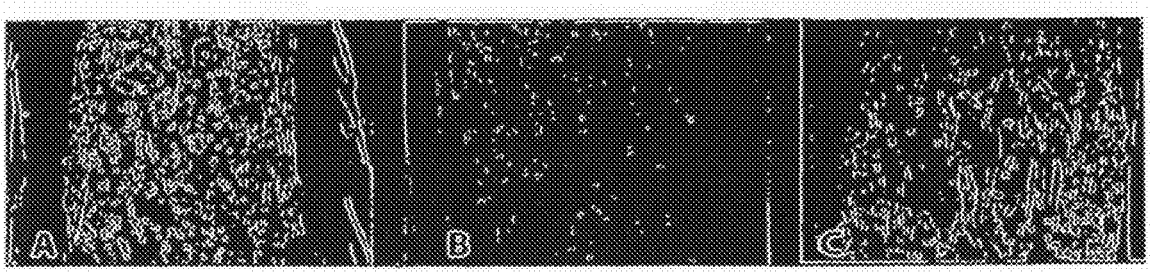
FIG. 11 is a series of micrographs showing histological (H&E) sections (10× magnification) comparing encapsulated cells after 2 week (FIG. 11A), 12 month (FIG. 11B), and 18 month (FIG. 11C) implantation periods.

Histological examination of explanted devices (FIG. 11) indicated stable encapsulated cell viability throughout the course of the 18 month implant period.

IL-10 Delivery

Figure 12:
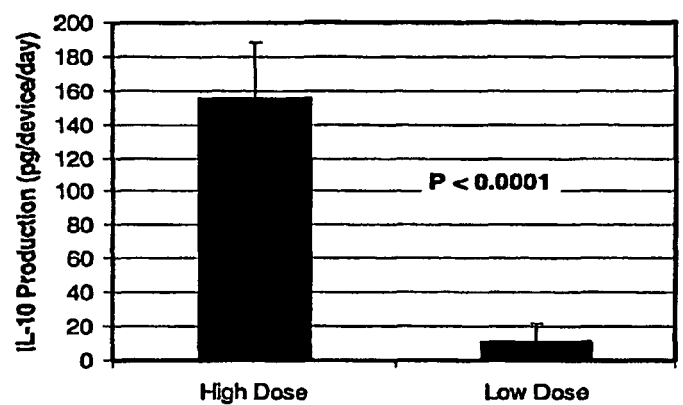
FIG. 12 is a histogram showing the dose delivery of interleukin-10 (IL-10) from micronized ECT devices.

Micronized ECT devices were implanted into the rat vitreous as part of a study to investigate treatment of experimental autoimmune uveoretinitis (EAU) delivered interleukin-10 ("IL-10") at either a pre-implant high dose of 156±32 (pg/device/day) or a low dose of 13±11 (pg/device/day) (FIG. 12).

Figure 13:
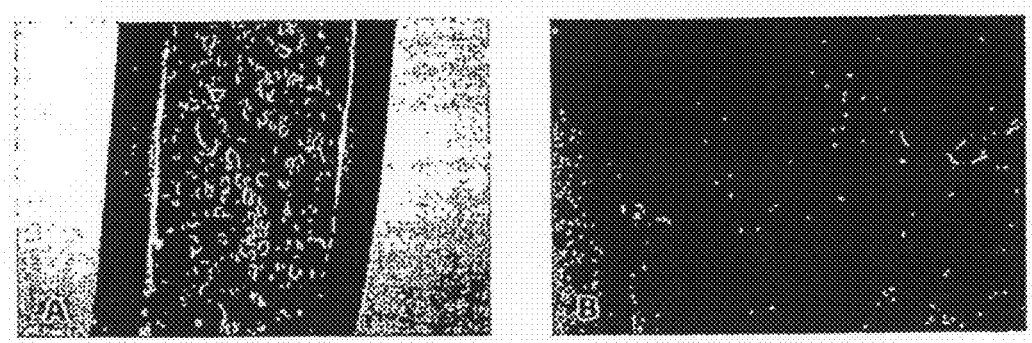
FIG. 13 is a series of photomicrographs of histological sections showing representative distribution (FIG. 13A) and viability (FIG. 13B) of encapsulated IL-10 producing cells in the micronized device.

Histological evaluation of the cells in the micronized ECT devices revealed robust viability and a high degree of cell distribution within the devices (FIG. 13). Preliminary results in the EAU model showed a beneficial treatment effect using ECT to deliver IL-10.

Throughout the course of these studies and regardless of animal models chosen for therapeutic delivery using ECT devices, no significant adverse post-operative complications were reported in any groups following periodic fundoscopy examinations.

Conclusions

Manufacture of ECT devices to deliver intravitreal levels of therapeutic molecules in both the rabbit (first generation devices) and rat (micronized devices) model was demonstrated. Both first generation and micronized implants were well tolerated and the delivery of therapeutics was continuous during the course of the entire implant period of up to 18 months.

Example 2

Delivery of Encapsulated Cell Technology (ECT) Micronized Device Implants Using a Small Gauge Needle Implantation of first generation ECT devices, which are currently in Phase II human clinical trials for retinitis pigmentosa and age-related macular degeneration, requires a 2.0 mm sclerotomy and three sutures to close the incision site. Thus, development of an ECT micronized device capable of producing comparable protein levels that could be implanted through a small gauge needle would improve the surgical procedure and minimize surgical risk.

Methods

Micronized devices were prepared that contained encapsulated cells transfected to produce either ciliary neurotrophic factor (CTNF), interleukin-10 (IL-10) or pigment epithelial derived factor (PEDF). Implantation of such micronized devices delivering CNTF was tested using a 23-gauge needle having a modified syringe. CNTF-producing devices were surgically implanted into New Zealand white rabbits and evaluated at 2 weeks and 1-month using indirect opthalmoscopy and histological examination. Two methods of closure were investigated: (1) incision closure using a 10-0 suture and needle attached to the device and (2) sutureless closure using a modified procedure to that described by Jaffe, et al, Arch Ophthalmol 114:1273-75 (1996) (incorporated herein by reference. Intravitreal CNTF levels, the production rate of explanted micronized devices and encapsulated cell viability were determined.

Results

Micronized devices produced 5.0±0.5, 3.0±0.7, and 39±4 ng/device/day of CNTF, IL-10 and PEDF, at the 2-week time point, respectively. Protein secretion from the micronized ECT devices was consistent and stable over the course of several months. Protein output to device volume levels were 10 times greater than the capacity of the first generation ECT devices.

Figure 14:
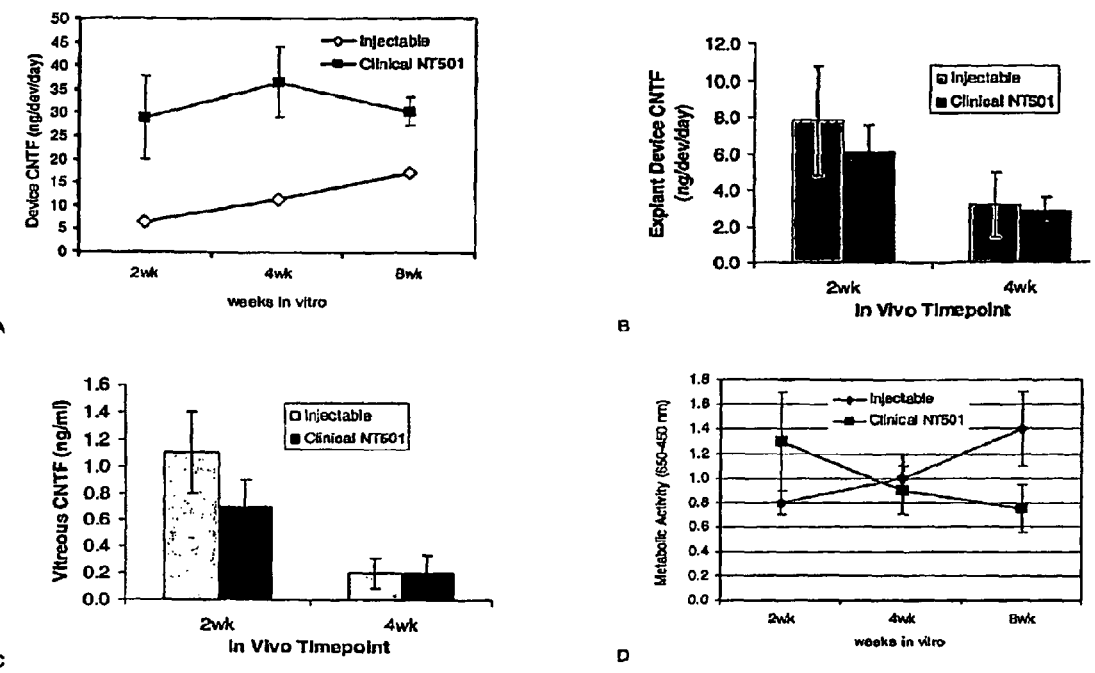
FIG. 14 is a series of graphs demonstrating first generation ECT and micronized ECT device performance.

Micronized device CNTF production was evaluated both in vitro and in vivo. First generation devices produced higher levels of CNTF during the in vitro evaluation period. (See FIG. 14A). However, 2 and 4-week explanted micronized CNTF levels were statistically equivalent (P=0.5663 and P=0.6744) to the levels produced by the first generation ECT devices. (See FIG. 14B). Moreover, vitreous CNTF levels were also statistically equivalent comparing the micronized device groups to the first generation device groups at both the 2 and 4-week in vivo evaluation time-points. (See FIG. 14C, P=0.2344 and P=0.8665, respectively). Metabolic activity of the micronized devices increased over time as compared to the first generation devices, which decreased over the 8 week in vitro hold period. (See FIG. 14D).

Figure 15:
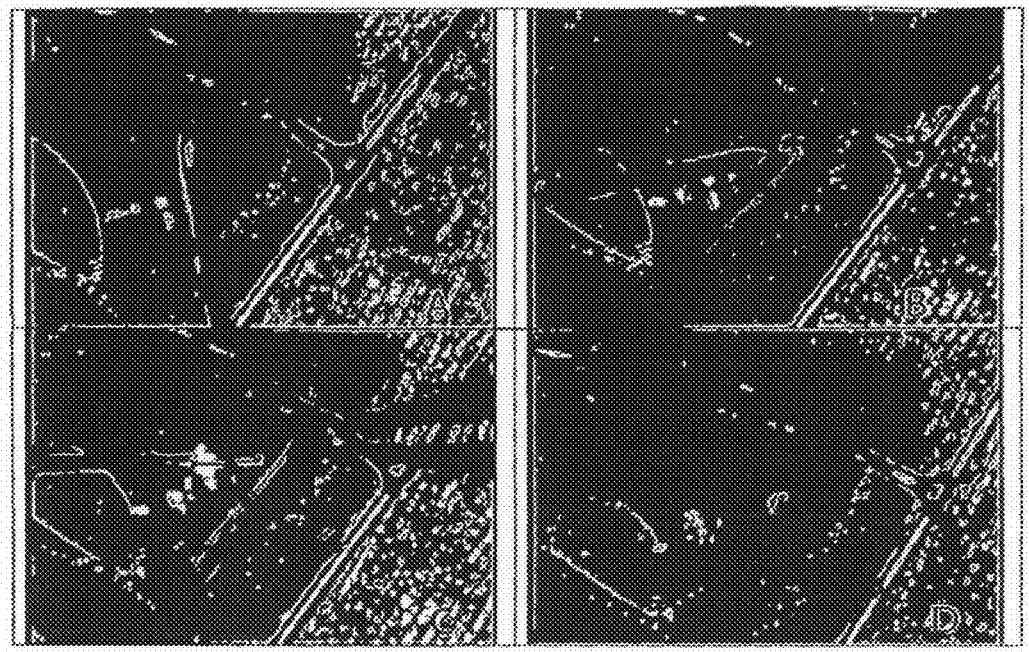
FIG. 15A is a photograph demonstrating micronized device implantation using a 23-gauge needle
FIG. 15B is a photograph that shows a 30° incision to the surface of the sclera through the pars plana.
FIG. 15C is a photograph that shows withdrawal of the . needle revealing inserted device with attached suture and needle.
FIG. 15D is a photograph that shows a single suture closure.

CNTF-producing micronized devices were injected successfully via a 23-gauge needle (see FIG. 15) and post-surgical evaluations of anchoring methods indicated successful placement and constraint of the micronized devices. The injectable sclerotomy closure was considerably less invasive and reduced the surgical time by half compared to implantation of the first generation ECT device.

Conclusions

Encapsulation using micronized devices can provide therapeutic protein levels comparable to the first generation device configuration currently used in ECT clinical trial evaluations. Likewise, surgical implantation of a micronized device using a 23-gauge needle to inject the devices appear to be feasible and may offer a simpler, less invasive approach to encapsulation cell therapy in the eye.

Example 3

Safety and Pharmacokinetics of an Injectable Micronized Encapsulated Cell Technology Device Three concurrent studies of a first generation encapsulated cell technology (ECT) device delivering ciliary neurotrophic factor (CNTF) are in human clinical for early and late-stage retinitis pigmentosa and age-related macular degeneration. ECT devices used in these trials are implanted in patients eyes using conjunctival excision, sceral incision, and inter-ocular placement followed by securing the device followed by suture closure of the sclera and conjunctiva. The current study reports on the research efforts to develop the long-term pharmacokinetics and safety profile of a smaller profile, nicronized ECT device capable of delivering efficacious therapeutics, implanted using sutureless, 23-gauge injection procedures.

Methods

Human retinal pigment epithelial cells genetically modified to continuously secrete CNTF were encapsulated in 300 micron diameter hollow fiber semi-permeable polymer membranes and delivered by inter-ocular implantation into the rabbit vitreous cavity. Implantation of the devices was performed using a modified version of the 23-gauge sutureless sclerotomy technique. Safety and CNTF protein pharmacokinetics over the course of a 1-year period are the eventual outcome endpoints of this study. Vitreous CNTF levels and explanted micronized device CNTF output were evaluated by a commercial ELISA.

Clinical and pathological evaluations were performed over the course of the implantation period in order to assess implant safety.

Results

At the three month time point, explanted micronized device production and vitreous levels of CNTF are 3.2 ng/day and 0.2 ng/ml, respectively. Preliminary fitted kinetics and half-life ($t_{1/2}$) constants for the explanted devices are $k=0.0167$ weeks$^{-1}$ and $t_{1/2}=41$ weeks, respectively. Vitreous level $k=0.036$ weeks$^{-1}$ and $t_{1/2}=19$ weeks. No evidence of ocular toxicity was observed in eyes that were implanted using the sutureless sclerotomy implant method. Clinical and pathohistological evaluation of the implant site showed normal wound healing response that was consistent with expected tissue reaction following surgical incision. Additionally, no adverse pan-retinal, optic nerve or vascular toxicity was observed in any of the implanted eyes.

Conclusions

Thus, preliminary results of this study indicate that micronized ECT devices are capable of sustaining long term intraocular delivery of CNTF in the rabbit. Additionally, the safety profile of a trans-conjunctival implant procedure that mitigates the necessity to suture the micronized device also shows promise for the potential of an injectable micronized ECT device.

We claim:

1. A method for delivering a biologically active molecule to the eye, the method comprising implanting at least one micronized device for delivery of a therapeutic dose of a biologically active molecule to the eye comprising a capsule into the eye or surrounding the eye and allowing said biologically active molecule to diffuse from the device into the vitreous, the aqueous humor, or the periocular space of the eye, wherein the capsule comprises:
   a) a core comprising between about $5\times10^2$ and $90\times10^3$ living cells that produce a biologically active molecule, wherein the biologically active molecule is selected from the group consisting of antiangiogenic factors, anti-inflammatory factors, neurotrophic factors, growth factors, trophic factors, antibodies and antibody fragments, neurotransmitters, hormones, cytokines, and lymphokines, wherein the core has a volume of less than 0.5 µl, and wherein the core further comprises a substantially non-degradable filamentous cell-supporting matrix, wherein the matrix comprises a plurality of monofilaments, wherein said monofilaments are twisted into a yarn or woven into a mesh or twisted into a yarn that is in non-woven strands, and wherein the cells are distributed thereon, and
   b) a biocompatible jacket surrounding said core, the jacket having a molecular weight cutoff permitting diffusion of the biologically active molecule into the eye,
wherein the device is configured as a cylinder with an outer diameter of between 200 and 350 µm and a length of between 0.5 and 6 mm, wherein the therapeutic dosage of the biologically active molecule that diffuses into the eye is between 0.1 pg and 1000 ng per eye per patient per day for a period greater than three months.

2. The method of claim 1, wherein the biologically active molecule is selected from the group consisting of TGFβ, GDNF, NGF, CNTF, bFGF, aFGF, IL-1β, IFN-β, IFN-α, BDNF, LIF, NT-4, NTN, NT4/5, CT-1, lens epithelium-derived growth factor (LEDGF), Neublastin, modified CNTF (AXOKINE®), IL-23, rod-derived cone viability factor (RdCVF), IL-10, Alpha INF, IL-1Rα, an antibody against tumor necrosis factor (REMICADE®), vasculostatin, angiostatin, endostatin, anti-integrins, vascular endothelial growth factor inhibitors (VEGF-inhibitors), platelet factor 4, heparinase, bFGF-binding molecules, the VEGF receptor Flt, the VEGF receptor Flk, an antibody against VEGF (LUCENTIS®), soluble VEGF Receptors, and PEDF.

3. The method of claim 1, wherein said at least one micronized device is implanted using a syringe.

4. A method for treating ophthalmic disorders in a patient suffering there from, comprising implanting a micronized device for delivery of a therapeutic dose of a biologically active molecule to the eye comprising a capsule into an eye of the patient, wherein the capsule comprises:
   a) a core comprising between about $5\times10^2$ and $90\times10^3$ living cells that produce a biologically active molecule, wherein the biologically active molecule is selected from the group consisting of CNTF and IL-10, wherein the core has a volume of less than 0.5 µl, wherein said monofilaments are twisted into a yarn or woven into a mesh or twisted into a yarn that is in non-woven strands, and wherein the cells are distributed thereon and
   b) a biocompatible jacket surrounding said core, the jacket having a molecular weight cutoff permitting diffusion of the biologically active molecule into the eye,
wherein the device is configured as a cylinder with an outer diameter of between 200 and 350 µm and a length of between 0.5 and 6 mm, wherein the therapeutic dosage of the biologically active molecule that diffuses into the eye is between 0.1 pg and 1000 ng per eye per patient per day for a period greater than three months, and wherein the ophthalmic disorder is selected from the group consisting of retinitis pigmentosa and experimental autoimmune uveoretinitis (EAU).

* * * * *